United States Patent [19]
Kajiwara et al.

[11] Patent Number: 5,910,433
[45] Date of Patent: Jun. 8, 1999

[54] KETO GROUP-INTRODUCING ENZYME, DNA CODING THEREFOR AND METHOD FOR PRODUCING KETOCAROTENOIDS

[75] Inventors: Susumu Kajiwara, Tokyo; Norihiko Misawa; Keiji Kondo, both of Kanagawa, all of Japan

[73] Assignee: Kirin Beer Kabushiki Kaisha, Tokyo, Japan

[21] Appl. No.: 08/632,434

[22] PCT Filed: Aug. 18, 1995

[86] PCT No.: PCT/JP95/01640

§ 371 Date: Apr. 23, 1996

§ 102(e) Date: Apr. 23, 1996

[87] PCT Pub. No.: WO96/06172

PCT Pub. Date: Feb. 29, 1996

[30] Foreign Application Priority Data

Aug. 23, 1994 [JP] Japan .................................. 6-198775
Sep. 19, 1994 [JP] Japan .................................. 6-223798
Mar. 7, 1995 [JP] Japan .................................. 7-047266

[51] Int. Cl.$^6$ .............................. C12P 7/26; C12N 9/02; C12N 1/12; C07H 21/04
[52] U.S. Cl. ........................... 435/148; 435/67; 435/189; 435/252.3; 435/252.33; 435/320.1; 435/946; 536/23.2; 536/24.3
[58] Field of Search ............................. 435/67, 188, 189, 435/252.3, 252.33, 320.1, 148, 946; 536/23.2, 24.3

[56] References Cited

FOREIGN PATENT DOCUMENTS

94/06918 9/1993 WIPO .
95/18220 9/1994 WIPO .

OTHER PUBLICATIONS

Yamano, et al. "Metabolic Engineering for Production of β–Carotene and Lycopene in *Saccharomyces cerevisiae*," *Biosci. Biotech. Biochem.* 58(6): 1112–14 (1994).
Anderson, et al. "Isopentenyl Diphosphate:Dimethylallyl Diphosphate Isomerase: An Improved Purification of The Enzyme and Isolation of the Gene from *Saccharomyces cerevisiae*," *J. of Biochem.* 264(32):19169–19175 (1989).
Misawa, et al. "Production of β–Carotene in *Zymomonas mobilis* and *Agrobacterium tumefaciens* by Introduction of the Biosysnthesis Genes from *Erwinia uredovora*," *Appl. Envirom, Microbiol.* 57(6):1847–49 (1991).
Misawa, et al. "Symposium Papers of 36th Symposium on the Chemistry of Natural Products," pp. 175–180 (1994).
"DNA Sequences Encoding Enzymes for Carotenoid Biosynthesis", Japanese patent 3–58786 (abstract).
"Carotenoids of *Erwinia Herbicola* and an *Escherichia Coli* HB101 Strain Carrying the *Erwinia Herbicola* Carotenoid Gene Cluster", Hundle et al., Photochem. and Photobiol., vol. 54., pp. 89–93 (1991).
"Elucidation of the *Erwinia Uredovora* Carotenoid Biosynthetic Pathway by Functional Analysis of Gene Products Expressed in *Escherichia Coli*", Misawa et al., J. of Bacteriology, Dec. 1990, pp. 6704–6712.
"Production of β–Carotene in Zymomonas Mobilis and Agrobacterium Tumefaciens by Introduction of the Biosynthesis Genes from *Erwinia Uredovora*", Applied and Environmental Microbiology, (Jun. 1991), vol. 57, pp. 1847–1849.
"Astaxanthin from Microbial Sources", Johnson et al., Critical Reviews in Biotechnology, vol. 11, pp. 297–326 (1991).
"Metabolic Engineering for Production of β–Carotene and Lycopene in *Saccharomyces Cerevisoiae*", Yamano et al., Biosci. Biotech. Biochem., vol. 58, pp. 1112–1114, (1994).
"Functional Complementation in *Escherichia Coli* of Different Phytoene Desaturase Genes and Analysis of Accumulated Carotenes", Linden et al., (1991) Z. Naturforsch, 46e, 1045–1051.
"Carotenoids of Phaffia Rhodozyma, A Red–Pigmented Fermenting Yeast", Andrewes et al., Phytochemistry, (1976). vol. 15, pp. 1003–1007.
"Genetic Analysis of Astaxanthin–Overproducting Mutants of Phaffia Rhodozyma Using RAPD's", BioTechnoloy Techniques, vol. 8, No. 1, (Jan. 1994), pp. 1–6.
"Cloning and Expression in *Escherichia Coli* of the Gene Encoding β–C–4–Oxygenase, that Converts β–Carotene to the Ketocarotenoid Canthaxanthin in *Haematococcus Pluvialis*", Lotan et al., FEBS Letters (1995) vol. 364, pp. 125–128.

*Primary Examiner*—Charles L. Patterson, Jr.
*Assistant Examiner*—Elizabeth Slobodyansky
*Attorney, Agent, or Firm*—Foley & Lardner

[57] ABSTRACT

DNA sequences are described that encode genes for synthesizing ketocarotenoids such as astaxanthin. The DNA sequences, microorganisms containing them and encoded polypeptides are described. Also described are methods to obtain related sequences and to make host cells that contain such sequences. These genes and methods are useful to impart red coloration during culture of fish and crustaceans, as coloring in food, and as antioxidants.

16 Claims, 12 Drawing Sheets

FIG. 1

```
A
▼       176         185         194         203         212         221
ATG CAC GTC GCA TCG GCA CTA ATG GTC GAG CAG AAA GGC AGT GAG GCA GCT GCT
Met His Val Ala Ser Ala Leu Met Val Glu Gln Lys Gly Ser Glu Ala Ala Ala
        230         239         248         257         266         275
TCC AGC CCA GAC GTC TTG AGA GCG TGG GCG ACA CAG TAT CAC ATG CCA TCC GAG
Ser Ser Pro Asp Val Leu Arg Ala Trp Ala Thr Gln Tyr His Met Pro Ser Glu
        284         293         302         311         320         329
TCG TCA GAC GCA GCT CGT CCT GCG CTA AAG CAC GCC TAC AAA CCT CCA GCA TCT
Ser Ser Asp Ala Ala Arg Pro Ala Leu Lys His Ala Tyr Lys Pro Pro Ala Ser
        338         347         356         365         374         383
GAC GCC AAG GGC ATC ACG ATG GCG CTG ACC ATC ATT GGC ACC TGG ACC GCA GTG
Asp Ala Lys Gly Ile Thr Met Ala Leu Thr Ile Ile Gly Thr Trp Thr Ala Val
        392         401         410         419         428         437
TTT TTA CAC GCA ATA TTT CAA ATC AGG CTA CCG ACA TCC ATG GAC CAG CTT CAC
Phe Leu His Ala Ile Phe Gln Ile Arg Leu Pro Thr Ser Met Asp Gln Leu His
        446         455         464         473         482         491
TGG TTG CCT GTG TCC GAA GCC ACA GCC CAG CTT TTG GGC GGA AGC AGC AGC CTA
Trp Leu Pro Val Ser Glu Ala Thr Ala Gln Leu Leu Gly Gly Ser Ser Ser Leu
        500         509         518         527         536         545
CTG CAC ATC GCT GCA GTC TTC ATT GTA CTT GAG TTC CTG TAC ACT GGT CTA TTC
Leu His Ile Ala Ala Val Phe Ile Val Leu Glu Phe Leu Tyr Thr Gly Leu Phe
        554         563         572         581         590         599
ATC ACC ACA CAT GAC GCA ATG CAT GGC ACC ATA GCT TTG AGG CAC AGG CAG CTC
Ile Thr Thr His Asp Ala Met His Gly Thr Ile Ala Leu Arg His Arg Gln Leu
        608         617         626         635         644         653
AAT GAT CTC CTT GGC AAC ATC TGC ATA TCA CTG TAC GCC TGG TTT GAC TAC AGC
Asn Asp Leu Leu Gly Asn Ile Cys Ile Ser Leu Tyr Ala Trp Phe Asp Tyr Ser
        662         671         680         689         698         707
ATG CTG CAT CGC AAG CAC TGG GAG CAC CAC AAC CAT ACT GGC GAA GTG GGG AAA
Met Leu His Arg Lys His Trp Glu His His Asn His Thr Gly Glu Val Gly Lys
        716         725         734         743         752         761
GAC CCT GAC TTC CAC AAG GGA AAT CCC GGC CTT GTC CCC TGG TTC GCC AGC TTC
Asp Pro Asp Phe His Lys Gly Asn Pro Gly Leu Val Pro Trp Phe Ala Ser Phe
        770         779         788         797         806         815
ATG TCC AGC TAC ATG TCC CTG TGG CAG TTT GCC CGG CTG GCA TGG TGG GCA GTG
Met Ser Ser Tyr Met Ser Leu Trp Gln Phe Ala Arg Leu Ala Trp Trp Ala Val
        824         833         842         851         860         869
GTG ATG CAA ATG CTG GGG GCG CCC ATG GCA AAT CTC CTA GTC TTC ATG GCT GCA
Val Met Gln Met Leu Gly Ala Pro Met Ala Asn Leu Leu Val Phe Met Ala Ala
        878         887         896         905         914         923
GCC CCA ATC TTG TCA GCA TTC CGC CTC TTC TAC TTC GGC ACT TAC CTG CCA CAC
Ala Pro Ile Leu Ser Ala Phe Arg Leu Phe Tyr Phe Gly Thr Tyr Leu Pro His
        932         941         950         959         968         977
AAG CCT GAG CCA GGC CCT GCA GCA GGC TCT CAG GTG ATG GCC TGG TTC AGG GCC
Lys Pro Glu Pro Gly Pro Ala Ala Gly Ser Gln Val Met Ala Trp Phe Arg Ala
        986         995         1004        1013        1022        1031
AAG ACA AGT GAG GCA TCT GAT GTG ATG AGT TTC CTG ACA TGC TAC CAC TTT GAC
Lys Thr Ser Glu Ala Ser Asp Val Met Ser Phe Leu Thr Cys Tyr His Phe Asp
        1040        1049        1058        1067        1076        1085
CTG CAC TGG GAG CAC CAC AGG TGG CCC TTT GCC CCC TGG TGG CAG CTG CCC CAC
Leu His Trp Glu His His Arg Trp Pro Phe Ala Pro Trp Trp Gln Leu Pro His
        1094        1103        1112        1121        1130
TGC CGC CGC CTG TCC GGG CGT GGC CTG GTG CCT GCC TTG GCA TGA
Cys Arg Arg Leu Ser Gly Arg Gly Leu Val Pro Ala Leu Ala ***
                                                        ▲
                                                        D
```

FIG. 2

B
▼
```
        197             206             215             224             233             242
ATG GTC GAG CAG AAA GGC AGT GAG GCA GCT GCT TCC AGC CCA GAC GTC TTG AGA
Met Val Glu Gln Lys Gly Ser Glu Ala Ala Ala Ser Ser Pro Asp Val Leu Arg
        251             260             269             278             287             296
GCG TGG GCG ACA CAG TAT CAC ATG CCA TCC GAG TCG TCA GAC GCA GCT CGT CCT
Ala Trp Ala Thr Gln Tyr His Met Pro Ser Glu Ser Ser Asp Ala Ala Arg Pro
        305             314             323             332             341             350
GCG CTA AAG CAC GCC TAC AAA CCT CCA GCA TCT GAC GCC AAG GGC ATC ACG ATG
Ala Leu Lys His Ala Tyr Lys Pro Pro Ala Ser Asp Ala Lys Gly Ile Thr Met
        359             368             377             386             395             404
GCG CTG ACC ATC ATT GGC ACC TGG ACC GCA GTG TTT TTA CAC GCA ATA TTT CAA
Ala Leu Thr Ile Ile Gly Thr Trp Thr Ala Val Phe Leu His Ala Ile Phe Gln
        413             422             431             440             449             458
ATC AGG CTA CCG ACA TCC ATG GAC CAG CTT CAC TGG TTG CCT GTG TCC GAA GCC
Ile Arg Leu Pro Thr Ser Met Asp Gln Leu His Trp Leu Pro Val Ser Glu Ala
        467             476             485             494             503             512
ACA GCC CAG CTT TTG GGC GGA AGC AGC AGC CTA CTG CAC ATC GCT GCA GTC TTC
Thr Ala Gln Leu Leu Gly Gly Ser Ser Ser Leu Leu His Ile Ala Ala Val Phe
        521             530             539             548             557             566
ATT GTA CTT GAG TTC CTG TAC ACT GGT CTA TTC ATC ACC ACA CAT GAC GCA ATG
Ile Val Leu Glu Phe Leu Tyr Thr Gly Leu Phe Ile Thr Thr His Asp Ala Met
        575             584             593             602             611             620
CAT GGC ACC ATA GCT TTG AGG CAC AGG CAG CTC AAT GAT CTC CTT GGC AAC ATC
His Gly Thr Ile Ala Leu Arg His Arg Gln Leu Asn Asp Leu Leu Gly Asn Ile
        629             638             647             656             665             674
TGC ATA TCA CTG TAC GCC TGG TTT GAC TAC AGC ATG CTG CAT CGC AAG CAC TGG
Cys Ile Ser Leu Tyr Ala Trp Phe Asp Tyr Ser Met Leu His Arg Lys His Trp
        683             692             701             710             719             728
GAG CAC CAC AAC CAT ACT GGC GAA GTG GGG AAA GAC CCT GAC TTC CAC AAG GGA
Glu His His Asn His Thr Gly Glu Val Gly Lys Asp Pro Asp Phe His Lys Gly
        737             746             755             764             773             782
AAT CCC GGC CTT GTC CCC TGG TTC GCC AGC TTC ATG TCC AGC TAC ATG TCC CTG
Asn Pro Gly Leu Val Pro Trp Phe Ala Ser Phe Met Ser Ser Tyr Met Ser Leu
        791             800             809             818             827             836
TGG CAG TTT GCC CGG CTG GCA TGG TGG GCA GTG GTG ATG CAA ATG CTG GGG GCG
Trp Gln Phe Ala Arg Leu Ala Trp Trp Ala Val Val Met Gln Met Leu Gly Ala
        845             854             863             872             881             890
CCC ATG GCA AAT CTC CTA GTC TTC ATG GCT GCA GCC CCA ATC TTG TCA GCA TTC
Pro Met Ala Asn Leu Leu Val Phe Met Ala Ala Ala Pro Ile Leu Ser Ala Phe
        899             908             917             926             935             944
CGC CTC TTC TAC TTC GGC ACT TAC CTG CCA CAC AAG CCT GAG CCA GGC CCT GCA
Arg Leu Phe Tyr Phe Gly Thr Tyr Leu Pro His Lys Pro Glu Pro Gly Pro Ala
        953             962             971             980             989             998
GCA GGC TCT CAG GTG ATG GCC TGG TTC AGG GCC AAG ACA AGT GAG GCA TCT GAT
Ala Gly Ser Gln Val Met Ala Trp Phe Arg Ala Lys Thr Ser Glu Ala Ser Asp
        1007            1016            1025            1034            1043            1052
GTG ATG AGT TTC CTG ACA TGC TAC CAC TTT GAC CTG CAC TGG GAG CAC CAC AGG
Val Met Ser Phe Leu Thr Cys Tyr His Phe Asp Leu His Trp Glu His His Arg
        1061            1070            1079            1088            1097            1106
TGG CCC TTT GCC CCC TGG TGG CAG CTG CCC CAC TGC CGC CGC CTG TCC GGG CGT
Trp Pro Phe Ala Pro Trp Trp Gln Leu Pro His Cys Arg Arg Leu Ser Gly Arg
        1115            1124
GGC CTG GTG CCT GCC TTG GCA TGA
Gly Leu Val Pro Ala Leu Ala ***
                              ▲
                              D
```

FIG. 3

C
↓
|       | 272 |     |     | 281 |     |     | 290 |     |     | 299 |     |     | 308 |     |     | 317 |
|-------|-----|-----|-----|-----|-----|-----|-----|-----|-----|-----|-----|-----|-----|-----|-----|-----|
| ATG | CCA | TCC | GAG | TCG | TCA | GAC | GCA | GCT | CGT | CCT | GCG | CTA | AAG | CAC | GCC | TAC | AAA |
| Met | Pro | Ser | Glu | Ser | Ser | Asp | Ala | Ala | Arg | Pro | Ala | Leu | Lys | His | Ala | Tyr | Lys |
|     | 326 |     |     | 335 |     |     | 344 |     |     | 353 |     |     | 362 |     |     | 371 |
| CCT | CCA | GCA | TCT | GAC | GCC | AAG | GGC | ATC | ACG | ATG | GCG | CTG | ACC | ATC | ATT | GGC | ACC |
| Pro | Pro | Ala | Ser | Asp | Ala | Lys | Gly | Ile | Thr | Met | Ala | Leu | Thr | Ile | Ile | Gly | Thr |
|     | 380 |     |     | 389 |     |     | 398 |     |     | 407 |     |     | 416 |     |     | 425 |
| TGG | ACC | GCA | GTG | TTT | TTA | CAC | GCA | ATA | TTT | CAA | ATC | AGG | CTA | CCG | ACA | TCC | ATG |
| Trp | Thr | Ala | Val | Phe | Leu | His | Ala | Ile | Phe | Gln | Ile | Arg | Leu | Pro | Thr | Ser | Met |
|     | 434 |     |     | 443 |     |     | 452 |     |     | 461 |     |     | 470 |     |     | 479 |
| GAC | CAG | CTT | CAC | TGG | TTG | CCT | GTG | TCC | GAA | GCC | ACA | GCC | CAG | CTT | TTG | GGC | GGA |
| Asp | Gln | Leu | His | Trp | Leu | Pro | Val | Ser | Glu | Ala | Thr | Ala | Gln | Leu | Leu | Gly | Gly |
|     | 488 |     |     | 497 |     |     | 506 |     |     | 515 |     |     | 524 |     |     | 533 |
| AGC | AGC | AGC | CTA | CTG | CAC | ATC | GCT | GCA | GTC | TTC | ATT | GTA | CTT | GAG | TTC | CTG | TAC |
| Ser | Ser | Ser | Leu | Leu | His | Ile | Ala | Ala | Val | Phe | Ile | Val | Leu | Glu | Phe | Leu | Tyr |
|     | 542 |     |     | 551 |     |     | 560 |     |     | 569 |     |     | 578 |     |     | 587 |
| ACT | GGT | CTA | TTC | ATC | ACC | ACA | CAT | GAC | GCA | ATG | CAT | GGC | ACC | ATA | GCT | TTG | AGG |
| Thr | Gly | Leu | Phe | Ile | Thr | Thr | His | Asp | Ala | Met | His | Gly | Thr | Ile | Ala | Leu | Arg |
|     | 596 |     |     | 605 |     |     | 614 |     |     | 623 |     |     | 632 |     |     | 641 |
| CAC | AGG | CAG | CTC | AAT | GAT | CTC | CTT | GGC | AAC | ATC | TGC | ATA | TCA | CTG | TAC | GCC | TGG |
| His | Arg | Gln | Leu | Asn | Asp | Leu | Leu | Gly | Asn | Ile | Cys | Ile | Ser | Leu | Tyr | Ala | Trp |
|     | 650 |     |     | 659 |     |     | 668 |     |     | 677 |     |     | 686 |     |     | 695 |
| TTT | GAC | TAC | AGC | ATG | CTG | CAT | CGC | AAG | CAC | TGG | GAG | CAC | CAC | AAC | CAT | ACT | GGC |
| Phe | Asp | Tyr | Ser | Met | Leu | His | Arg | Lys | His | Trp | Glu | His | His | Asn | His | Thr | Gly |
|     | 704 |     |     | 713 |     |     | 722 |     |     | 731 |     |     | 740 |     |     | 749 |
| GAA | GTG | GGG | AAA | GAC | CCT | GAC | TTC | CAC | AAG | GGA | AAT | CCC | GGC | CTT | GTC | CCC | TGG |
| Glu | Val | Gly | Lys | Asp | Pro | Asp | Phe | His | Lys | Gly | Asn | Pro | Gly | Leu | Val | Pro | Trp |
|     | 758 |     |     | 767 |     |     | 776 |     |     | 785 |     |     | 794 |     |     | 803 |
| TTC | GCC | AGC | TTC | ATG | TCC | AGC | TAC | ATG | TCC | CTG | TGG | CAG | TTT | GCC | CGG | CTG | GCA |
| Phe | Ala | Ser | Phe | Met | Ser | Ser | Tyr | Met | Ser | Leu | Trp | Gln | Phe | Ala | Arg | Leu | Ala |
|     | 812 |     |     | 821 |     |     | 830 |     |     | 839 |     |     | 848 |     |     | 857 |
| TGG | TGG | GCA | GTG | GTG | ATG | CAA | ATG | CTG | GGG | GCG | CCC | ATG | GCA | AAT | CTC | CTA | GTC |
| Trp | Trp | Ala | Val | Val | Met | Gln | Met | Leu | Gly | Ala | Pro | Met | Ala | Asn | Leu | Leu | Val |
|     | 866 |     |     | 875 |     |     | 884 |     |     | 893 |     |     | 902 |     |     | 911 |
| TTC | ATG | GCT | GCA | GCC | CCA | ATC | TTG | TCA | GCA | TTC | CGC | CTC | TTC | TAC | TTC | GGC | ACT |
| Phe | Met | Ala | Ala | Ala | Pro | Ile | Leu | Ser | Ala | Phe | Arg | Leu | Phe | Tyr | Phe | Gly | Thr |
|     | 920 |     |     | 929 |     |     | 938 |     |     | 947 |     |     | 956 |     |     | 965 |
| TAC | CTG | CCA | CAC | AAG | CCT | GAG | CCA | GGC | CCT | GCA | GCA | GGC | TCT | CAG | GTG | ATG | GCC |
| Tyr | Leu | Pro | His | Lys | Pro | Glu | Pro | Gly | Pro | Ala | Ala | Gly | Ser | Gln | Val | Met | Ala |
|     | 974 |     |     | 983 |     |     | 992 |     |     | 1001|     |     | 1010|     |     | 1019|
| TGG | TTC | AGG | GCC | AAG | ACA | AGT | GAG | GCA | TCT | GAT | GTG | ATG | AGT | TTC | CTG | ACA | TGC |
| Trp | Phe | Arg | Ala | Lys | Thr | Ser | Glu | Ala | Ser | Asp | Val | Met | Ser | Phe | Leu | Thr | Cys |
|     | 1028|     |     | 1037|     |     | 1046|     |     | 1055|     |     | 1064|     |     | 1073|
| TAC | CAC | TTT | GAC | CTG | CAC | TGG | GAG | CAC | CAC | AGG | TGG | CCC | TTT | GCC | CCC | TGG | TGG |
| Tyr | His | Phe | Asp | Leu | His | Trp | Glu | His | His | Arg | Trp | Pro | Phe | Ala | Pro | Trp | Trp |
|     | 1082|     |     | 1091|     |     | 1100|     |     | 1109|     |     | 1118|     |     | 1127|
| CAG | CTG | CCC | CAC | TGC | CGC | CGC | CTG | TCC | GGG | CGT | GGC | CTG | GTG | CCT | GCC | TTG | GCA |
| Gln | Leu | Pro | His | Cys | Arg | Arg | Leu | Ser | Gly | Arg | Gly | Leu | Val | Pro | Ala | Leu | Ala |

TGA
---
***

```
                                  30                                      60
CGGGGCAACT CAAGAAATTC AACAGCTGCA AGCGCGCCCC AGCCTCACAG CGCCAAGTGA
GCCCCGTTGA GTTCTTTAAG TTGTCGACGT TCGCGCGGGG TCGGAGTGTC GCGGTTCACT
                                  90                                     120
GCTATCGACG TGGTTGTGAG CGCTCGACGT GGTCCACTGA CGGGCCTGTG AGCCTCTGCG
CGATAGCTGC ACCAACACTC GCGAGCTGCA CCAGGTGACT GCCCGGACAC TCGGAGACGC
                                                     A
                                 150                 ▼                   180
CTCCGTCCTC TGCCAAATCT CGCGTCGGGG CCTGCCTAAG TCGAAGAATG CACGTCGCAT
GAGGCAGGAG ACGGTTTAGA GCGCAGCCCC GGACGGATTC AGCTTCTTAC GTGCAGCGTA
          B
          ▼                      210                                     240
CGGCACTAAT GGTCGAGCAG AAAGGCAGTG AGGCAGCTGC TTCCAGCCCA GACGTCTTGA
GCCGTGATTA CCAGCTCGTC TTTCCGTCAC TCCGTCGACG AAGGTCGGGT CTGCAGAACT
                 C
                 ▼               270                                     300
GAGCGTGGGC GACACAGTAT CACATGCCAT CCGAGTCGTC AGACGCAGCT CGTCCTGCGC
CTCGCACCCG CTGTGTCATA GTGTACGGTA GGCTCAGCAG TCTGCGTCGA GCAGGACGCG
                                 330                                     360
TAAAGCACGC CTACAAACCT CCAGCATCTG ACGCCAAGGG CATCACGATG GCGCTGACCA
ATTTCGTGCG GATGTTTGGA GGTCGTAGAC TGCGGTTCCC GTAGTGCTAC CGCGACTGGT
                                 390                                     420
TCATTGGCAC CTGGACCGCA GTGTTTTAC ACGCAATATT TCAAATCAGG CTACCGACAT
AGTAACCGTG GACCTGGCGT CACAAAAATG TGCGTTATAA AGTTTAGTCC GATGGCTGTA
                                 450                                     480
CCATGGACCA GCTTCACTGG TTGCCTGTGT CCGAAGCCAC AGCCCAGCTT TTGGGCGGAA
GGTACCTGGT CGAAGTGACC AACGGACACA GGCTTCGGTG TCGGGTCGAA AACCCGCCTT
                                 510                                     540
GCAGCAGCCT ACTGCACATC GCTGCAGTCT TCATTGTACT TGAGTTCCTG TACACTGGTC
CGTCGTCGGA TGACGTGTAG CGACGTCAGA AGTAACATGA ACTCAAGGAC ATGTGACCAG
                                 570                                     600
TATTCATCAC CACACATGAC GCAATGCATG GCACCATAGC TTTGAGGCAC AGGCAGCTCA
ATAAGTAGTG GTGTGTACTG CGTTACGTAC CGTGGTATCG AAACTCCGTG TCCGTCGAGT
                                 630                                     660
ATGATCTCCT TGGCAACATC TGCATATCAC TGTACGCCTG GTTTGACTAC AGCATGCTGC
TACTAGAGGA ACCGTTGTAG ACGTATAGTG ACATGCGGAC CAAACTGATG TCGTACGACG
                                 690                                     720
ATCGCAAGCA CTGGGAGCAC CACAACCATA CTGGCGAAGT GGGGAAAGAC CCTGACTTCC
TAGCGTTCGT GACCCTCGTG GTGTTGGTAT GACCGCTTCA CCCCTTTCTG GGACTGAAGG
                                 750                                     780
ACAAGGGAAA TCCCGGCCTT GTCCCTGGT TCGCCAGCTT CATGTCCAGC TACATGTCCC
TGTTCCCTTT AGGGCCGGAA CAGGGGACCA AGCGGTCGAA GTACAGGTCG ATGTACAGGG
                                 810                                     840
TGTGGCAGTT TGCCCGGCTG GCATGGTGGG CAGTGGTGAT GCAAATGCTG GGGGCGCCCA
ACACCGTCAA ACGGGCCGAC CGTACCACCC GTCACCACTA CGTTTACGAC CCCCGCGGGT
```

FIG. 5

```
                              870                            900
TGGCAAATCT CCTAGTCTTC ATGGCTGCAG CCCCAATCTT GTCAGCATTC CGCCTCTTCT
ACCGTTTAGA GGATCAGAAG TACCGACGTC GGGGTTAGAA CAGTCGTAAG GCGGAGAAGA 930                            960
ACTTCGGCAC TTACCTGCCA CACAAGCCTG AGCCAGGCCC TGCAGCAGGC TCTCAGGTGA
TGAAGCCGTG AATGGACGGT GTGTTCGGAC TCGGTCCGGG ACGTCGTCCG AGAGTCCACT 990                           1020
TGGCCTGGTT CAGGGCCAAG ACAAGTGAGG CATCTGATGT GATGAGTTTC CTGACATGCT
ACCGGACCAA GTCCCGGTTC TGTTCACTCC GTAGACTACA CTACTCAAAG GACTGTACGA 1050                           1080
ACCACTTTGA CCTGCACTGG GAGCACCACA GGTGGCCCTT TGCCCCCTGG TGGCAGCTGC
TGGTGAAACT GGACGTGACC CTCGTGGTGT CCACCGGGAA ACGGGGACC ACCGTCGACG 1110                           1140
CCCACTGCCG CCGCCTGTCC GGGCGTGGCC TGGTGCCTGC CTTGGCATGA CCTGGTCCCT
GGGTGACGGC GGCGGACAGG CCCGCACCGG ACCACGGACG GAACCGTACT GGACCAGGGA
                                                    ▲
                             1170                D          1200
CCGCTGGTGA CCCAGCGTCT GCACAAGAGT GTCATGCTAC AGGGTGCTGC GGCCAGTGGC
GGCGACCACT GGGTCGCAGA CGTGTTCTCA CAGTACGATG TCCCACGACG CCGGTCACCG 1230                           1260
AGCGCAGTGC ACTCTCAGCC TGTATGGGGC TACCGCTGTG CCACTGAGCA CTGGGCATGC
TCGCGTCACG TGAGAGTCGG ACATACCCCG ATGGCGACAC GGTGACTCGT GACCCGTACG 1290                           1320
CACTGAGCAC TGGGCGTGCT ACTGAGCAAT GGGCGTGCTA CTGAGCAATG GCGTGCTAC
GTGACTCGTG ACCCGCACGA TGACTCGTTA CCCGCACGAT GACTCGTTAC CCGCACGATG 1350                           1380
TGACAATGGG CGTGCTACTG GGTCTGGCA GTGGCTAGGA TGGAGTTTGA TGCATTCAGT
ACTGTTACCC GCACGATGAC CCCAGACCGT CACCGATCCT ACCTCAAACT ACGTAAGTCA 1410                           1440
AGCGGTGGCC AACGTCATGT GGATGGTGGA AGTGCTGAGG GGTTTAGGCA GCCGGCATTT
TCGCCACCGG TTGCAGTACA CCTACCACCT TCACGACTCC CCAAATCCGT CGGCCGTAAA 1470                           1500
GAGAGGGCTA AGTTATAAAT CGCATGCTGC TCATGCGCAC ATATCTGCAC ACAGCCAGGG
CTCTCCCGAT TCAATATTTA GCGTACGACG AGTACGCGTG TATAGACGTG TGTCGGTCCC 1530                           1560
AAATCCCTTC GAGAGTGATT ATGGGACACT TGTATTGGTT TCGTGCTATT GTTTTATTCA
TTTAGGGAAG CTCTCACTAA TACCCTGTGA ACATAACCAA AGCACGATAA CAAAATAAGT 1590                           1620
GCAGCAGTAC TTAGTGAGGG TGAGAGCAGG GTGGTGAGAG TGGAGTGAGT GAGTATGAAC
CGTCGTCATG AATCACTCCC ACTCTCGTCC CACCACTCTC ACCTCACTCA CTCATACTTG 1650                           1677
CTGGTCAGCG AGGTGAACAG CCTGTAATGA ATGACTCTGT CTAAAAAAAA AAAAAAA
GACCAGTCGC TCCACTTGTC GGACATTACT TACTGAGACA GATTTTTTTT TTTTTTT
```

FIG. 11

```
           10         20         30         40         50         60
    CGGGGCAACT CAAGAAATTC AACAGCTGCA AGCGCGCCCC AGCCTCACAG CGCCAAGTGA 70         80         90        100        110        120
    GCTATCGACG TGGTTGTGAG CGCTCGACGT GGTCCACTGA CGGGCCTGTG AGCCTCTGCG
                                                    A           ↳30
          130        140        150        160       ▼170        180
    CTCCGTCCTC TGCCAAATCT CGCGTCGGGG CCTGCCTAAG TCGAAGAATG CACGTCGCAT
      ↳27    B
             ▼190        200        210        220        230        240
    CGGCACTAAT GGTCGAGCAG AAAGGCAGTG AGGCAGCTGC TTCCAGCCCA GACGTCTTGA
                      C                              ↳31
          250        260     ▼  270        280        290        300
    GAGCGTGGGC GACACAGTAT CACATGCCAT CCGAGTCGTC AGACGCAGCT CGTCCTGCGC
    ↳37                        ↳12
          310        320        330        340        350        360
    TAAAGCACGC CTACAAACCT CCAGCATCTG ACGCCAAGGG CATCACGATG GCGCTGACCA
         ↳10                  ↳6
          370        380        390        400        410        420
    TCATTGGCAC CTGGACCGCA GTGTTTTTAC ACGCAATATT TCAAATCAGG CTACGACAT
                               ↳38
          430        440        450        460        470        480
    CCATGGACCA GCTTCACTGG TTGCCTGTGT CCGAAGCCAC AGCCCAGCTT TTGGGCGGAA
```

KETO GROUP-INTRODUCING ENZYME, DNA CODING THEREFOR AND METHOD FOR PRODUCING KETOCAROTENOIDS

FIELD OF THE INVENTION

The present invention relates to a keto group-introducing enzyme necessary for synthesizing ketocarotenoids, such as astaxanthin, which are useful for a red-color enhancing treatment of cultured fishes and shellfishes (such as sea bream, salmon and shrimp) and are also applied to foods as a coloring agent or an antioxidant; a DNA coding for the above enzyme; a recombinant vector comprising the DNA; a microorganism into which the DNA has been introduced; and a method for producing ketocarotenoids using the above microorganism.

BACKGROUND ART

"Ketocarotenoid" is a general term for keto group-containing carotenoid pigments. Carotenoids are synthesized from mevalonic acid as a starting substance via isoprenoid basic biosynthesis pathway which shares an initial part with the synthesis pathway for steroids and other isoprenoids (see FIG. 6). Isopentenyl pyrophosphate (IPP) with 5 carbon atoms, which is a basic unit, generated from the isoprenoid basic biosynthesis pathway condenses with its isomer dimethylallyl pyrophosphate (DMAPP) to produce geranyl pyrophosphate (GPP) with 10 carbon atoms and, in addition, IPP condenses to produce farnesyl pyrophosphate (FPP) with 15 carbon atoms. FPP produces geranylgeranyl pyrophosphate (GGPP) with 20 carbon atoms by condensing with IPP again. Then, GGPPs condense with each other to produce colorless phytoene which is the initial carotenoid. Through a series of unsaturated reactions, phytoene is converted to phytofluene, ζ-carotene, neurosporene and finally to lycopene. Subsequently, lycopene is converted by a cyclization reaction to a β-carotene containing two β-ionone rings. Finally, it is believed that a keto-groups, a hydroxyl group, etc. are introduced into the β-carotene to thereby synthesize astaxanthin, zeaxanthin and the like (see Britton, G., "Biosynthesis of Carotenoids", Plant Pigments, Goodwin, T. W (ed.), London, Academic Press, 1988, pp. 133–182).

Recently, the present inventors have cloned a group of carotenoid biosynthesis genes of the non-photosynthetic bacterium *Erwinia uredovora* present in plant from the genomic DNA library in *E. coli* using its yellow color formation as an indicator. Further, by expressing a various combinations of these genes in microorganisms such as *E. coli*, the inventors has made it possible to produce in microorganisms such as *E. coli* phytoene, lycopene, β-carotene and zeaxanthin which is a yellow carotenoid pigment wherein a hydroxyl group has been introduced into β-carotene (see FIG. 7) (Misawa, N., Nakagawa, M., Kobayashi, K., Yamano, S., Izawa, Y., Nakamura, K., and Harashima, K., "Elucidation of the *Erwinia uredovora* Carotenoid Biosynthetic Pathway by Functional Analysis of Gene Products Expressed in *Escherichia coli*", J. Bacteriol., 172, pp. 6704–6712, 1990; Misawa, N., Yamano, S, Ikenaga, H., "Production of βcarotene in *Zymomonas mobilis* and *Agrobacterium tumefaciens* by Introduction of the Biosynthesis Genes from *Erwinia uredovora*", Appl. Environ. Microbiol., 57, pp. 1847–1849, 1991; and Japanese Unexamined Patent Publication No. 3-58786).

On the other hand, astaxanthin which is a red ketokarotenoid is a representative animal carotenoid widely present in marine organisms, e.g. red fishes such as sea bream and salmon, and crustaceans such as crab and shrimp. Since animals generally cannot biosynthesize carotenoids, they have to take in from outside those catotenoids synthesized by microorganisms or plants. For this reason, astaxanthin has been widely used for the purpose of red color enhancing for cultured fishes and shellfishes such as sea bream, salmon and shrimp.

Astaxanthin is also used as a coloring agent for foods. Furthermore, astaxanthin is attracting attention as an antioxidant to remove activated oxygen generated in a body which is causative of a cancer (see Takao Matuno and Wataru Inui, "Physiological Functions and Biological Activities of Carotenoids in Animals", KAGAKU TO SEIBUTU (Chemistry and Organisms), 28, pp. 219–227, 1990).

As sources of astaxanthin supply, there are known crustaceans such as antarctic krill, a culture of the yeast Phaffia, a culture of the green alga Haematococcus and compounds which are obtained by organic synthesis. However, when crustaceans such as antarctic krill are used, it is difficult to separate astaxanthin from various contaminants, such as lipids, in a recovery and extraction process, which requires a great labor and cost. When a culture of the yeast Phaffia is used, the recovery and extraction of astaxanthin also requires a great cost since its cell wall is rigid and yet the production level of astaxanthin is low. In the case of using a culture of the green alga Haematococcus, it is necessary to supply to the alga during its cultivation some light which is essential for astaxanthin synthesis. Therefore, appropriate conditions on a location for taking sun light in or cultivation facilities capable of supplying artificial light are required. In addition, it is difficult to separate the produced astaxanthin from mixed up chlorophyl and by-products (fatty acid esters). For these reasons, it has been true that the organism-derived astaxanthin described above cannot compete with those obtained by organic synthesis in cost. However, considering that astaxanthin is used as feed for fishes and shellfishes and as a food additive, an astaxanthin prepared by organic synthesis has some problems with respect to by-products produced in the reaction and yet such an astaxanthin is against the consumers' liking for natural products.

Under circumstances, the development of a method for producing an organism-derived cheap astaxanthin which is safe and can meet the consumers' liking for natural products is desired.

Then, it is believed that the acquisition of a group of genes involved in the biosynthesis of astaxanthin would be very useful, because it is possible to render an optimal microorganism with respect of safety as a food and a potential ability to produce astaxanthin, regardless of whether it has an ability to produce astaxanthin or not, the production ability by introducing into the microorganism the group of astaxanthin synthesis genes and expressing them. In this case, there will occur no problem of the mixing of by-products. In addition, by using techniques of the highly advanced genetic engineering, it will not be difficult to increase the amount of astaxanthin production to a level which exceeds the production amount by organic synthesis. As described above, a group of genes to synthesize up to zeaxanthin have already been obtained by the present inventors from the non-photosynthetic bacterium *Erwinia uredovora*. However, no one has succeeded in obtaining the gene coding for a keto group-introducing enzyme that is necessary for synthesizing astaxanthin, though a number of attempts have been made in many research institute because of the industrial utility of astaxanthin as described above. As to the reasons, it is considered that enzymes located downstream and involved in carotenoid biosynthesis, such as a keto group-introducing enzyme, are membrane proteins and that the purification and measurement of activity of those enzymes have been impossible; therefore, there has been no finding about those enzymes. In particular, as to a keto group-introducing enzyme, not only findings about the enzyme itself but also findings about the gene coding for the enzyme have not been reported at all. Therefore, to date, it has been impossible to produce astaxanthin in a microorganism or the like by using genetic engineering techniques.

DISCLOSURE OF THE INVENTION

Accordingly, it is an object of the invention to provide the gene coding for a keto group-introducing enzyme which is necessary for producing ketocarotenoids containing keto groups, such as astaxanthin.

It is another object of the invention to provide a keto group-introducing enzyme.

It is still another object of the invention to provide a recombinant vector comprising the gene coding for the keto group-introducing enzyme.

Further, it is still another object of the invention to provide a microorganism into which the gene coding for the keto group-introducing enzyme have been introduced.

Further, it is still another object of the invention to provide a method for producing ketocarotenoids by using the above microorganism into which the gene coding for the keto group-introducing enzyme have been introduced.

The present inventors have made extensive and intensive researces toward solution of the above assignment and, as a result, have succeeded in cloning from the cDNA of the green alga Haematococcus the gene coding for a keto group-introducing enzyme, preparing a vector DNA incorporating the gene, introducing the vector DNA into E. coli, culturing the resultant E. coli in a medium, then collecting the cells from the medium, and extracting ketocarotenoids such as echinenone, canthaxanthin, astaxanthin, 4-ketozeaxanthin and the like. The present invention has been thus achieved. In other words, the invention provides a polypeptide having an enzyme activity to convert the methylene group at position 4 of a β-ionone ring to a keto group. The invention also provides a DNA comprising a base sequence coding for a polypeptide having an enzyme activity to convert the methylene group at position 4 of a β-ionone ring to a keto group. Further, the invention provides a recombinant vector comprising the above DNA. The invention also provides a microorganism into which the above DNA has been introduced. In addition, the invention provides a method for producing ketocarotenoids, comprising culturing in a medium the microorganism into which the DNA has been introduced and extracting ketocarotenoids from the culture cells.

Hereinbelow, the present invention will be described in more detail.

1. Keto group-introducing enzyme

The keto group-introducing enzyme of the invention is a polypeptide having an enzyme activity to convert the methylene group at position 4 of a β-ionone ring to a keto group. This polypeptide may be a polypeptide comprising the amino acid sequence substantially as shown in SEQ ID NO: 4 of the sequence listing (the amino acid sequence from A to D shown in FIG. 1), the amino acid sequence substantially as shown in SEQ ID NO: 6 (the amino acid sequence from B to D shown in FIG. 2) or the amino acid sequence substantially as shown in SEQ ID NO: 8 (the amino acid sequence from C to D shown in FIG. 3). The expression "the amino acid sequence substantially as shown in SEQ ID NO: 4, SEQ ID NO: 6 or SEQ ID NO: 8 of the sequence listing" used here means an amino acid sequence which may have variations such as deletion, substitution, addition, etc. in some of the amino acid residues in the sequence as shown in SEQ ID NO: 4, SEQ ID NO: 6 or SEQ ID NO: 8 of the sequence listing as long as such an amino acid sequence has the enzyme activity to convert the methylene group at position 4 of a β-ionone ring to a keto group, as well as the amino acid sequence as shown in SEQ ID NO: 4, SEQ ID NO: 6 or SEQ ID NO: 8. For example, an amino acid sequence wherein the first amino acid residue (Met) in SEQ ID NO: 4, SEQ ID NO: 6 or SEQ ID NO: 8 of the sequence listing is deleted is included in the above expression.

In one embodiment, the keto group-introducing enzyme of the invention is able to synthesize canthaxanthin via echinenone using β-carotene as a substrate. Also, the enzyme of the invention can convert the methylene group at position 4 of 3-hydroxy-β-ionone ring to a keto group. As one specific example of the above, the enzyme of the invention can synthesize astaxanthin via 4-ketozeaxanthin using zeaxanthin as a substrate (see FIG. 8). Since β-carotene and zeaxanthin, which are carotenoids, contain two molecules of β-ionone rings in one molecule, first the methylene group at position 4 of one β-ionone ring is converted to a keto group to produce echinenone and 4-ketozeaxanthin, respectively, and then the methylene group at position 4' (equivalent to position 4) of the other β-ionone ring is converted to a keto group to produce canthaxanthin and astaxanthin, respectively.

2. Keto group-introducing enzyme gene (bkt)

The gene coding for the keto group-introducing enzyme of the invention (hereinafter referred to as "bkt") is a DNA comprising a base sequence coding for a polypeptide having an enzyme activity to convert the methylene group at position 4 of a β-ionone ring to a keto group. A typical example of this gene is a bkt gene which can be cloned from the green alga *Haematococcus pluvialis* (NIES-144). This is a DNA comprising a base sequence coding for a polypeptide comprising the amino acid sequence which is substantially shown from A to D in FIG. 1 (the amino acid sequence as shown in SEQ ID NO: 4 of the sequence listing), the amino acid sequence which is substantially shown from B to D in FIG. 2 (the amino acid sequence as shown in SEQ ID NO: 6 of the sequence listing), or the amino acid sequence which is substantially shown from C to D in FIG. 3 (the amino acid sequence as shown in SEQ ID NO: 8 of the sequence listing). Examples for the base sequences coding for the amino acid sequences as shown in SEQ ID NO: 4, SEQ ID NO: 6 and SEQ ID NO: 8 of the sequence listing are given in SEQ ID NOS: 1 and 3, 5 and 7, respectively. The base sequence shown in SEQ ID NO: 1 includes a non-coding region in the upstream of the base sequence shown in SEQ ID NO: 3 which is a coding region. Needless to say, the bkt gene of the invention includes not only the DNAs comprising the base sequences shown in SEQ ID NOS: 1, 3, 5 and 7, but also those DNAs comprising a degenerate isomer coding for the same polypeptide which is different only in degenerate codons.

The bkt gene product (hereinafter referred to as "BKT"), i.e., the keto group-introducing enzyme of the present invention has, as described above, an enzyme activity to convert the methylene group at position 4 of a β-ionone ring in a compound containing β-ionone rings to a keto group. In one embodiment, BKT can synthesize canthaxanthin via echinenone using β-carotene as a substrate (see FIG. 8). Further, BKT can also convert the methylene group at position 4 of 3-hydroxy-β-ionone ring to a keto group. For example, BKT can synthesize astaxanthin via 4-ketozeaxanthin using zeaxanthin as a substrate (see FIG. 8). A polypeptide having such an enzyme activity and the DNA coding for it have not been known. This polypeptide and the DNA coding therefor do not have an overall homology with any of the polypeptides and DNAs which have been known to date. In addition, not limited to the conversion in a β-ionone ring or 3-hydroxy-β-ionone ring, there has been no finding that one enzyme converts a methylene group immediately to a keto group.

On the other hand, by using the carotenoid synthesis gene group of crtE, crtB, crti and crtY from the non-photosynthetic bacteria Erwinia, it is possible to render a microorganism such as *E. coli* an ability to produce β-carotene. By using crtZ gene in addition to the above four genes, it is possible to render a microorganism such as *E. coli* an ability to produce zeaxanthin (see FIG. 7 and WO91/13078, supra).

Accordingly, since β-carotene and zeaxanthin (which are substrates for BKT) are supplied by these crt gene group from Erwinia, when the DNA of the invention (bkt gene) is further introduced to a microorganism such as *E. coli* carrying the crt gene group from Erwinia, it will become possible for a β-carotene producing microorganism to produce canthaxanthin via echinenone and for a zeaxanthin producing microorganism to produce astaxanthin via 4-ketozeaxanthin (see FIG. 8). However, in a zeaxanthin producing microorganism, β-cryptoxanthin is contained in an extremely small amount as an intermediate. Therefore, in addition to the major metabolic pathway described above, there may be another pathway producing astaxanthin from β-cryptoxanthin via 3-hydroxyechinenone and 4-ketozeaxanthin, and still another pathway producing phoenicoxanthin from β-cryptoxanthin via 3-hydroxyechinenone or 3'-hydroxyechinenone. As products of these minor pathways, it is considered that 3'-hydroxyechinenone, 3-hydroxyechinenone and phoenicoxanthin can be produced (see FIG. 9).

3. Acquisition of the DNA

One means to obtain the DNA comprising a base sequence coding for an amino acid sequence of the keto group-introducing enzyme (BKT) of the invention is to chemically synthesize at least a portion of the DNA chain according to the conventional nucleic acid synthesizing methods. However, considering the length of sequence, it is preferable not to use the chemical synthesis but to obtain mRNA from the green algae Haematococcus (*Haematococcus pluvialis* and *Haematococcus lacustris* are representative varieties), prepare a cDNA library therefrom using *E. coli*, and obtain the DNA from this library by conventional methods used in the field of genetic engineering, e.g., the hybridization method with appropriate probes or the expression cloning method which the inventors have employed.

Specifically, the total RNA of *Haematococcus pluvialis* is separated and poly $A^+$ RNA is purified using Oligotex-dT30 Super (Takara Shuzo). Using this poly $A^+$ RNA as a template, cDNA is synthesized with the reverse transcriptase Superscript RT (Gibco BRL) and then double-stranded cDNA is synthesized with *E. coli* DNA ligase, *E. coli* DNA polymerase and *E. coli* DNA RNase H (all manufactured by (Gibco BRL). The synthesized cDNA is incorporated in an *E. coli* expression vector pSPORT1 (Gibco BRL) and a cDNA library is prepared. Using this cDNA library, a β-carotene producing *E. coli* (*E. coli* carrying the crt gene group of Erwinia as described above) is transformed. From the changes in color tone in the resultant transformants, those microorganisms carrying the keto group-introducing enzyme gene are screened. This method utilizes the phenomenon that the color tone of *E. coli* changes from a β-carotene-derived yellow to a canthaxanthin-derived red when a keto group has been introduced and canthaxanthin, one of ketocarotenoids, has been synthesized. From the transformed red *E. coli* thus obtained, a plasmid having a cDNA of interest is isolated and the cDNA is re-linked to *E. coli* vectors pBluescript II SK+ and pBluescript II KS+ (Stratagene). With these plasmids, deletion variants having various lengths of deletions are produced and the base sequences of the variants are determined.

4. DNAs which hybridize with the bkt gene

To date, several varieties of the green algae Haematococcus have been isolated and identified, and all of them are considered to synthesize ketocarotenoids such as astaxanthin. In yeast, *Phaffia rhodozyma* which is also an eucaryote has been reported to synthesize ketocarotenoids such as astaxanthin (Johnson, E. A. and An, G.-Hwan, "Astaxanthin from Microbial Sources", Critical Reviews in Biotechnology, 11, pp. 297–326, 1991). It is possible to obtain other genes of keto group-introducing enzymes from the above astaxanthin producing algae or microorganisms by using as a probe the *Haematococcus pluvialis* NIES-144 bkt gene as described above and carrying out hybridization by utilizing their homology. The present inventors have selected from those Haematococcus capable of synthesizing astaxanthin two varieties which are different from *Haematococcus pluvialis* NIES-144 in assimilation property and phenotype against light. They are *Haematococcus lacustris* UTEX 294 (released from the Culture Collection of Algae at the University of Texas at Austin) and *Haematococcus lacustris* C-392 [released from the Microorganisms and Microalgae Center belonging to the Applied Microorganism Laboratory (the current Molecular Cell Biology Laboratory), the University of Tokyo]. The genomic DNAs from these varieties were prepared and Southern hybridization was conducted using as a probe the *Haematococcus pluvialis* NIES-144 bkt gene. The results were as expected by the inventors. The bkt probe strongly hybridized with specific DNA fragments derived from either of the genomic DNA. Therefore, the present invention includes those DNAs which hybridize with the above-described DNAs (SEQ ID NOS: 1, 3, 5 and 7).

5. Transformation of a microorganism such as *E. coli*

By introducing the DNA of the invention as a foreign gene into an appropriate microorganism such as bacteria (e.g., *E. coli, Zymomonas mobilis, Agrobacterium tumefaciens*), yeast (e.g., *Saccharomyces cerevisiae*), etc. and expressing it, various ketocarotenoids can be produced.

Hereinbelow, the method for introducing a foreign gene into a preferable microorganism will be described briefly. With respect to procedures or methods for introducing a foreign gene into a microorganism such as *E. coli* and expressing the gene, conventional ones used in the field of genetic engineering may be used, as well as the procedures described herein. For example, procedures or methods according to those described in "Vectors for Cloning Genes", Methods in Enzymology, 216, pp. 469–631, 1992, Academic Press and "Other Bacterial Systems", Methods in Enzymology, 204, pp. 305–636, 1991, Academic Press may be used.

<Introduction of the gene into *E. coli*>

As a method for introducing a foreign gene into *E. coli*, there are several established, effective methods which may be used, such as Hanahan's method and the rubidium method (see, for example, Chapter 1, pp. 74–84, Sambrook, J., Fritsch, E. F., Maniatis, T., "Molecular Cloning, A Laboratory Manual", Cold Springs Harbor Laboratory Press, 1989). For the expression of a foreign gene in *E. coli*, it is preferable, for example, to introduce into *E. coli* a lac promoter-containing *E. coli* expression vector into which the foreign gene has been inserted according to conventional methods (see, for example, Chapter 17, pp. 3–41, "Molecular Cloning, A Laboratory Manual" supra ). The present inventors have inserted the Haematococcus bkt gene into the *E. coli* cDNA expression vector pSPORT1 (Gibco BRL) having a lac promoter etc. in a direction so that the inserted gene undergoes a read through of the transcription of the lac promoter, and then introduced the resultant vector into *E. coli*.

<Introduction of the gene into yeast>

As a method for introducing a foreign gene into the yeast *Sacchromyces cerevisiae*, there are established methods such as the lithium method which may be used (for example, see "KOHBONO NYUHBAIOTEKUNOROJIH (New Biotechnology of Yeast)" edited by the Bioindustry Association under the supervision of Y. Akiyama, published by Igaku Shuppan Center). For the expression of a foreign gene in yeast, it is preferable to construct an expression cassette using a promoter and a terminator such as PGK and GPD, in which cassette the foreign gene is inserted between the promoter and the terminator so that the gene undergoes a read through of the transcription. Then, this expression cassette is inserted into a vector for *S. cerevosiae*, for example, YRp system vector (a yeast multicopy vector making the ARS sequence in yeast chromosomes as a replication origin), YEp system vector (a yeast multicopy vector having a replication origin of yeast 2 $\mu$m DNA), YIp system vector (a vector to be incorporated in yeast chromosomes, not having a replication origin of yeast), etc. and the resultant vector is introduced into the yeast (see "New Biotechnology of Yeast", supra; Japan Agricultural & Horticultural Chemistry Association ABC Series "BUSSHITU SEISAN NOTAMENO IDENSHIKOU-GAKU (Genetic Engineering for the Production of Substances)", Asakura Shoten Co., Ltd.; and Yamano, S., Ishii, T., Nakagawa, M., Ikenaga, H., and Misawa, N., "Metabolic Engineering for Production of β-carotene and Lycopene in *Sacchromyces cerevisiae*", Biosci. Biotech. Biochem., 58, pp. 1112–1114, 1994).

<Introduction of the gene into *Zymomonas mobilis*>

The introduction of a foreign gene into the ethanol producing bacterium *Zymomonas mobilis* can be achieved by the conjugative transfer method which is commonly used for Gram-negative bacteria. For the expression of a foreign gene in *Zymomonas mobilis*, it is preferable, for example, to introduce into *Zymomonas mobilis* an expression vector into which the foreign gene has been inserted (e.g., vector pZA22 for *Zymomonas mobilis*) (see Nakamura, K., "Molecular Breeding of Zymomonas Bacteria", Journal of Japan Agricultural & Horticultural Chemistry Association, 63, pp. 1016–1018, 1989; and Misawa, N., Yamano, S, Ikenaga, H., "Production of β-carotene in *Zymomonas mobilis* and *Agrobacterium tumefaciens* by Introduction of the Biosynthesis Genes from *Erwinia uredovora*", Appl. Environ. Microbiol., 57, pp. 1847–1849, 1991).

<Introduction of the gene into *Agrobacterium tumefaciens*>

The introduction of a foreign gene into the plant pathogenic bacterium *Agrobacterium tumefaciens* can be achieved by the conjugative transfer method which is commonly used for Gram-negative bacteria. For the expression of a foreign gene in *Agrobacterium tumefaciens*, it is preferable, for example, to introduce into *Agrobacterium tumefaciens* an expression vector into which the foreign gene has been inserted (e.g., vector pBI121 for *Agrobacterium tumefaciens*) (see Misawa, N., Yamano, S, Ikenaga, H., "Production of β-carotene in *Zymomonas mobilis* and *Agrobacterium tumefaciens* by Introduction of the Biosynthesis Genes from *Erwinia uredovora*", Appl. Environ. Microbiol., 57, pp. 1847–1849, 1991).

6. Production of ketocarotenoids by microorganisms (expression of the bkt gene)

By using the techniques or methods as described above to introduce a foreign gene into a microorganism, it is possible to introduce into a microorganism a Haematococcus-derived group of ketocarotenoid (including astaxanthin) synthesis genes and express them.

Farnesyl pyrophosphate (FPP) is not only a substrate of carotenoids but is also a common substrate of other isoprenoids such as sesquiterpene, triterpene, sterol, hopanol, etc. Generally, microorganisms including those which cannot synthesize carotenoids synthesize other isoprenoids. Therefore, basically every microorganism is supposed to have FPP as an intermediary metabolite. On the other hand, using FPP as a substrate, the carotenoid synthesis gene group of the non-photosynthetic Erwinia is able to synthesize the substrates of the Haematococcus bkt gene product, i.e., up to β-carotene and zeaxanthin (see FIG. 7). The present inventors have introduced the Erwinia crt gene group not only into *E. coli* but also the microorganisms described above, (i.e. the yeast *Saccharomyces cerevisiae*, the ethanol producing bacterium *Zymomonas mobilis* and the plant pathogenic bacterium *Agrobacterium tumefaciens*) and confirmed that these microorganism have become able to produce carotenoids such as β-carotene as expected (see Yamano, S., Ishii, T., Nakagawa, M., Ikenaga, H., and Misawa, N., "Metabolic engineering for production of β-carotene and lycopene in *Saccharomyces cerevisiae*", Biosci., Biotech. Biochem., 58, p. 1112–1114, 1994; Misawa, N., Yamano, S, Ikenaga, H., "Production of β-carotene in *Zymomonas mobilis* and *Agrobacterium tumefaciens* by introduction of the biosynthesis genes from *Erwinia uredovora*", Appl. Environ. Microbiol., 57, pp. 1847–1849, 1991; and Japanese Unexamined Patent Publication No. 3-58786).

Accordingly, by introducing a combination of Erwinia-derived carotenoid synthesis genes with the DNA of the invention (which is typically the Haematococcus-derived carotenoid synthesis gene bkt) into the same microorganism simultaneously, it becomes possible to produce ketocarotenoids such as astaxanthin in all of those microorganisms wherein a gene introduction/expression system has been established. Alternatively, by introducing the DNA of the invention into a microorganism which inherently has carotenoid synthesis genes or a microorganism into which carotenoid synthesis genes have been already introduced, it is also possible to produce ketocarotenoids in the above microorganism. Hereinbelow, the production of various ketocarotenoids by microorganisms will be described.

<Production of canthaxanthin and echinenone>

By introducing into a microorganism, such as *E. coli*, the *Erwinia uredovora* crtE, crtB, crti and crtY genes necessary for the synthesis of β-carotene and the Haematococcus bkt gene which is a keto group-introducing enzyme gene and expressing them, it is possible to allow the microorganism to produce canthaxanthin as a final product. Furthermore, by regulating the level of expression of the bkt gene or the like, echinenone which is a synthetic intermediate can also be obtained. For example, in order to produce canthaxanthin and echinenone in *E. coli*, both a first plasmid (e.g., pAC-CAR16Δ crtX) obtainable by inserting into an *E. coli* vector (e.g., pACYC184) a fragment containing the *Erwinia uredovora* crtE, crtB, crtI and crtY genes and a second plasmid [e.g., pHP51 (see FIG. 10)] obtainable by inserting into an *E. coli* vector (e.g., pBluescript II KS+) a fragment containing the Haematococcus bkt gene are introduced into *E. coli* (e.g., JM101). The resultant *E. coli* is cultured in LB medium, 2YT medium or the like containing ampicillin and chloramphenicol under culture conditions at 30–37° C. until the stationary phase. Then, cells are harvested and carotenoid pigments are extracted by using an organic solvent such as acetone. Canthaxanthin and echinenone may be contained in the carotenoid pigments thus obtained.

<Production of astaxanthin and 4-ketozeaxanthin>

By introducing into a microorganism, such as *E. coli*, the *Erwinia uredovora* crtE, crtB, crtI, crtY and crtZ genes necessary for the synthesis of zeaxanthin and the Haematococcus bkt gene which is a keto group-introducing enzyme gene and expressing them, it is possible to allow the microorganism to produce astaxanthin as a final product. Furthermore, by regulating the level of expression of the bkt gene or the like, 4-ketozeaxanthin which is a synthetic intermediate can also be obtained. For example, in order to produce astaxanthin and 4-ketozeaxanthin in *E. coli*, both a first plasmid (e.g., pACCAR25Δ crtX) obtainable by inserting into an *E. coli* vector (e.g., pACYC184) a fragment containing the *Erwinia uredovora* crtE, crtB, crtI, crtY and crtZ genes and a second plasmid (e.g., pHP51) obtainable by inserting into an *E. coli* vector (e.g., pBluescript II KS+) a fragment containing the Haematococcus bkt gene are introduced into *E. coli* (e.g., JM101). The resultant *E. coli* is cultured in, for example, LB medium or 2YT medium containing ampicillin and chloramphenicol under culture conditions at 30–37° C. until the stationary phase. Then, cells are harvested and carotenoid pigments are extracted by using an organic solvent such as acetone. Astaxanthin and 4-ketozeaxanthin may be contained in the carotenoid pigments thus obtained.

<Production of 3'-hydroxyechinenone, 3-hydroxyechinenone and phoenicoxanthin>

By introducing into a microorganism, such as *E. coli*, the *Erwinia uredovora* crtE, crtB, crtI, crtY and crtZ genes necessary for the synthesis of zeaxanthin and the Haematococcus bkt gene which is a keto group-introducing enzyme gene and expressing them, it is possible to allow the microorganism to produce astaxanthin and 4ketozeaxanthin as major products. However, as minor intermediary metabolites, 3'-hydroxyechinenone, 3-hydroxyechinenone and phoenicoxanthin should be present in the pathway.

Methods for producing these pigments are similar to those methods described above. For details, see the Examples.

7. Deposit of the microorganism

The *E. coli* DH5a into which plasmid pHP51 incorporating the isolated bkt gene (i.e., the DNA of the invention) has been introduced was deposited at the National Institute of Bioscience and Human-technology, Agency of Industrial Science and Technology, as follows:

Designation for identification assigned by the depositor: DH5α (pHP51)

Accession Number: FERM BP-4757

Date of Deposit: Jul. 26, 1994

BRIEF DESCRIPTION OF DRAWINGS

FIG. 1 shows the base sequence of a keto group-introducing enzyme gene (bkt) from the green alga *Haematococcus pluvialis* NIES-144 and the amino acid sequence of a polypeptide encoded by the above base sequence (SEQ ID NOS:3 and 4).

FIG. 2 shows the base sequence of a keto group-introducing enzyme gene (bkt) from the green alga *Haematococcus Pluvialis* NIES-144 and the amino acid sequence of a polypeptide encoded by the base sequence (SEQ ID NOS:5 and 6).

FIG. 3 shows the base sequence of a keto group-introducing enzyme gene (bkt) from the green alga *Haematococcus pluvialis* NIES-144 and the amino acid sequence of a polypeptide encoded by the base sequence (SEQ ID NOS:7–8).

In FIGS. 1 to 3 above, the initiation codons are different ones.

FIG. 4 shows the base sequence of a DNA chain comprising a keto group-introducing enzyme gene (bkt) from the green alga *Haematococcus pluvialis* NIES-144). A, B and C in the FIG. show the positions of the initiation codons (bases 1–840 of SEQ ID NO:1 are shown in this figure).

FIG. 5 shows a sequence which follows the one shown in FIG. 4 (bases 841–1677 of SEQ ID NO:1 are shown in this figure).

pHP5 is inserted into pSPORT I and pHP51 into pBluescript II KS+ in such a direction that they undergo the read-through of the lac promoter. The sites digested by restriction enzymes are abbreviated as follows: S, SalI; Ss, SstI; P, PstI; Sp, SphI; N, NotI; X, XbaI; K. KpnI; Sa, SacI.

FIG. 11 shows the base sequence for a region including the initiation codons of the keto group-introducing enzyme gene (bkt) from the green alga *Haematococcus pluvialis* NIES-144 and indicates the initiation sites of various deletion plasmids (bases 1–480 of SEQ ID NO:1 are shown in this figure).

Figure 12:
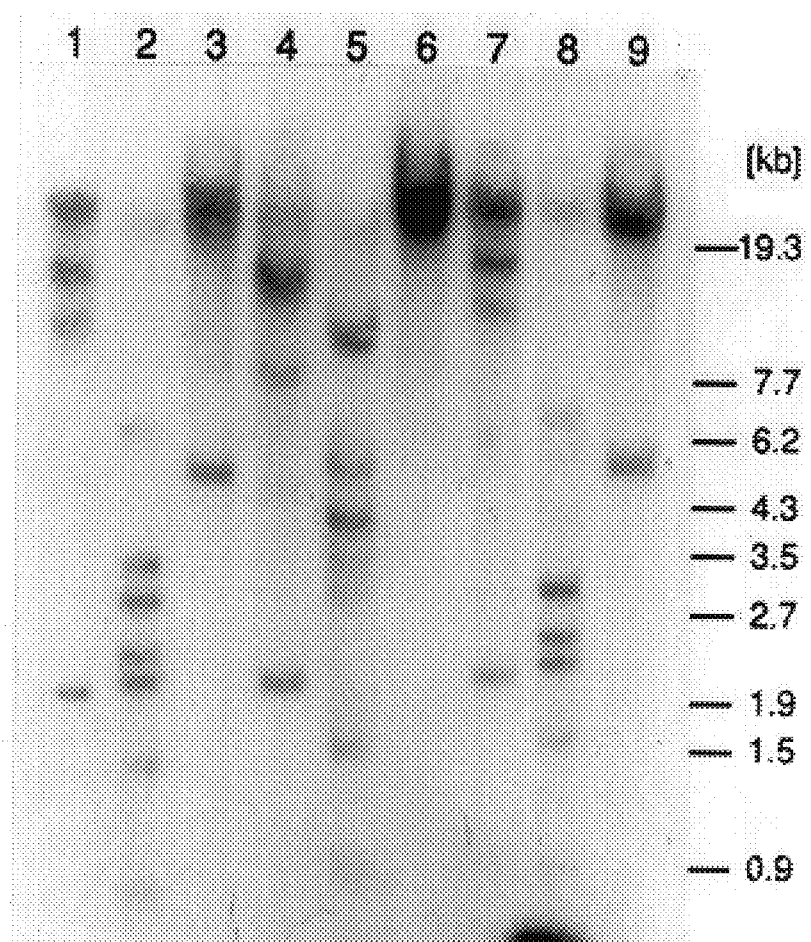

FIG. 12 shows the results of Southern analysis (electrophoresis photo) using as a probe a 1.7 kb DNA fragment of the green alga *Haematococcus pluvialis* NIES-144 bkt gene.

Lanes 1–3: *Haematococcus pluvialis* NIES-144
Lanes 4–6: *Haematococcus lacustris* UTEX294
Lanes 7–9: *Haematococcus lacustris* C392
Lanes 1, 4 and 7: HindIII digest
Lanes 2, 5 and 8: PstI digest
Lanes 3, 6 and 9: XbaI digest

BEST MODES FOR CARRYING OUT THE INVENTION

The present invention will be described more specifically below with reference to the following Examples, which should not be construed as limiting the scope of the invention.

[EXAMPLE 1]

Biomaterials and the Medium Composition

The *Haematococcus pluvialis* used for obtaining genes is the NIES-144 strain registered at the Foundation Global Environmental Forum. *H. pluvialis* was cultured for 4 days in basal medium (yeast extract 0.2%; sodium acetate 0.12%; L-asparagine 0.04%; magnesium chloride.$6H_2O$ 0.02%; iron(II) sulfate.$7H_2O$ 0.001%; calcium chloride.$2H_2O$ 0.002%) at 20° C. under 12 hr light/12 hr dark cycles (20 $\mu E/m^2 \cdot s$). Further, for the induction of astaxanthin synthesis in *H. pluvialis*, acetic acid was added to the *H. pluvialis* NIES-144 strain to a final concentration of 45 mM and iron(II) sulfate. $7H_2O$ to a final concentration of 450 $\mu m$, and the strain was cultured at 20° C. at a photointensity of 125 $\mu E/m^2 \cdot s$ for about 12 hours to thereby induce the formation of cysts.

[EXAMPLE 2]

Preparation of the Total DNA from *Haematococcus pluvialis*

The *H. pluvialis* NIES-144 strain was seeded on 400 ml of basal medium and cultured at 20° C. at a photointensity of 20 $\mu E/m^2 \cdot s$ under 12 hr light/12 hr dark cycles for about 4 days. Then, cells were harvested from the culture, frozen with liquefied nitrogen and crushed in a mortar until the cells became powder-like. To the powder-like cells, 15 ml of extraction buffer (0.1M Tris-Hcl pH 8.0, 0.1M EDTA, 0.25M NaCl, 0.1 mg/ml Proteinase K) was added, stirred violently and then kept at 55° C. for 2 hours. Then, the mixture was centrifuged at 6000×g for 10 minutes at 4° C. to remove the precipitate. To the supernatant, 0.6 volume of isopropanol was added and cooled at −20° C. for 30 minutes. Then, the mixture was centrifuged at 7500×g for 15 minutes at 4° C. The centrifuged material containing DNA was dissolved in 2 ml of TE buffer (10 mM Tris-HCl pH 8.0, 1 mM EDTA), mixed with the same volume of phenol:chloroform (1:1) and then subjected to centrifugation to extract the upper layer. Subsequently, 80 $\mu l$ of 5 M NaCl and 5 mL of ethanol were added to the upper layer, cooled at −20° C. for 30 minutes and then centrifuged at 12000×g for 15 minutes at 4° C. The precipitate was rinsed with 70% ethanol and then dried. Thereafter, the precipitate was dissolved in 0.5 ml of TE buffer (10 mM Tris-HCl pH 8.0, 1 mM EDTA) and 2.5 $\mu l$ of 10 mg/ml RNase A was added thereto to make a total DNA solution of *Haematococcus pluvialis*.

[EXAMPLE 3]

Attempt to Isolate crtZ Homologous Regions from *H. pluvialis* by PCR

By comparing amino acid sequences encoded by crtZ genes from *Erwinia uredovora* and *Erwinia herbicola* (Misawa, N., Nakagawa, M., Kobayashi, K., Yamano, S., Izawa, Y., Nakamura, K. and Harashima, K., "Elucidation of the *Erwinia uredovora* carotenoid biosynthetic pathway by functional analysis of gene products expressed in *Escherichia coli*", J. Bacteriol., 172, pp. 6704–6712, 1990; Hundle, B. S., Beyer, P., Kleinig, H., Englert, G. and Hearst, J. E., "Carotenoids of *Erwinia herbicola* and an *Escherichia coli* HB101 strain carrying the *Erwinia herbicola* Carotenoid Gene Cluster", Phytochem. Phytobiol., 54, pp. 89–93, 1991), regions with a high homology were found out. By combining those codons which are expected to be used in view of the amino acid sequences of these regions, the following 3 primers were synthesized to prepare mixed primers.

No. 1 5'-GGNTGGGGNTGGCAYAARTCNCAYCA-3' (SEQ ID NO:9)

No. 2 5'-CANCGYTGRTGNACNAGNCCRTCRTG-3' (SEQ ID NO:10)

No. 3 5'-GCRTASATRAANCCRAARCTNACRCA-3' (SEQ ID NO:11)

[N: A, G, C or T; R: A or G; Y: C or T; S: A, G or T]

A mixed primer consisting of No. 1 & No. 2 (SEQ ID NOS:9 and 10) and another mixed primer consisting of No. 1 & No. 3 (SEQ ID NOS:9 and 12) were prepared and PCR (polymerase chain reaction) was carried out using the total DNA solution of *H. pluvialis* as templates. The following materials were mixed so that they have the following final concentrations: about 100 ng total DNA solution of *H. pluvialis*; each 100 $\mu m$ mixed primers; 1×Vent Buffer [10 mM KCl, 20 mM Tris-HCl (pH 8.8), 10 mM $(NH_4)_2SO_4$, 2 mM $MgSO_4$, 0.1% Triton X-100); 250 $\mu M$ dNTP; and 2 U Vent DNA polymerase (New England Biolabs, Inc.). The PCR was conducted 30 cycles with the conditions of at 94° C. for 30 seconds, 55° C. for 30 seconds and 72° C. for 30 seconds, and 30 cycles with the conditions of at 94 ° C. for 30 seconds, 60° C. for 30 seconds and 72° C. for 30 seconds. Then, the presence of reaction products was confirmed by electrophoresis. However, in any of the cases, a definite, single product has not been detected.

[EXAMPLE 4]

Preparation of the Total RNA from *Haematococcus pluvialis*

The *H. pluvialis* NIES-144 strain was seeded on 800 ml of basal medium and cultured at 20° C. at a photointensity of 20 $\mu E/m^2 \cdot s$ under 12 hr light/12 hr dark cycles for about 4 days. Then, acetic acid was added thereto to give a final concentration of 45 mM and iron(II) sulfate.$7H_2O$ to a final concentration of 450 $\mu m$. Thereafter, cells were cultured at 20° C. at a photointensity of 125 $\mu E/m^2 \cdot s$ for about 12 hours. Then, cells were harvested from the culture, frozen with liquefied nitrogen and crushed in a mortar until the cells became powder-like. To the powder-like cells, 3 ml of ISOGEN-LS (Nippon Gene) was added and left at room temperature for 5 minutes. Further, 0.8 ml of chloroform was added thereto. The mixture was violently stirred for 15 seconds and then left at room temperature for 3 minutes. The resultant mixture was centrifuged at 12000×g for 15 minutes at 4° C. to extract the upper layer. To the upper layer, 2 ml of isopropanol was added and left at room temperature for 10 minutes. Then, the mixture was centrifuged at 12000×g for 10 minutes at 4° C. Subsequently, the precipitate was rinsed with 70% ethanol, dried and then dissolved in 1 ml of TE buffer (10 mM Tris-HCl pH 8.0, 1 mM EDTA) to obtain a total RNA solution of *Haematococcus pluvialis*. By the above procedures, 4.1 mg of the total RNA was obtained.

[EXAMPLE 5]

Preparation of the cDNA Expression Library of *Haematococcus pluvialis*

Using Oligotex-dT30 Super (Takara Shuzo), poly A+ RNA was purified from approximately 1 mg of the total RNA of H. pluvialis according to the manufacture's protocol attached to the product. Approximately 14 μg of poly A+ mRNA was purified by this method.

cDNA was prepared by using Superscript TM Plasmid System (Gibco BRL) according to the attached protocol with a partial modification as follows. By using approximately 5 μg of poly A+ RNA, a complementary DNA strand was synthesized with a synthetic DNA comprising the recognition sequence of the restriction enzyme NotI and an oligo-dT of 15-mers as a primer. Subsequently, by using E. coli DNA ligase, E. coli DNA polymerase and E. coli DNA RNase H, a double-stranded cDNA was synthesized. To this cDNA, the linker of the restriction enzyme SalI was ligated with T4 DNA ligase so that finally the upstream end of this cDNA would be a SalI site and the downstream of poly A an NotI site. The cDNAs obtained were fractionated by size by electrophoresis and the fractions containing fragments ranging from 0.7 kb to 3.5 kb were collected. About 28 ng of the cDNAs of these fractions and 35 ng of the cDNA expression vector pSPORT I (Gibco BRL) which was digested with NotI and SalI were ligated with the ligation buffer (50 mM Tris-HCl pH 7.6, 10 mM MgCl$_2$, 1 mM ATP, 1 mM DTT, 5% PEG 8000) contained in the above-described kit and T4 DNA ligase. This cDNA expression vector pSPORT I is a vector having a lac promoter upstream of a SalI site and capable of expressing a cDNA in E. coli. Then, using all of the ligated DNA solution, transformation of competent cells of the E. coli DH5α which were prepared according to the method described in Molecular Cloning (2nd edition): Cold Spring Harbor Laboratory, 1.21–1.41 (1989) was carried out. About 40,000 strains of transformants were obtained. Collecting all of these transformants, plasmid DNA was prepared according to the method described in Molecular Cloning (2nd edition): Cold Spring Harbor Laboratory, 1.21–1.41 (1989). As a result, 0.6 mg of plasmid DNA was obtained and this was made the cDNA expression library of Haematococcus pluvialis.

[EXAMPLE 6]

Screening Utilizing the Changes of Color Tone in the Keto Group-Introducing Enzyme Gene Carrying E. coli (1) Preparation of β-carotene producing E. coli By subjecting plasmid pCAR16 which contains all of the Erwinia uredovora carotenoid synthesis genes (crtE, crtX, crtY, crtI and crtB) other than crtZ (see Misawa, N., Nakagawa, M., Kobayashi, K., Yamano, S., Izawa, Y., Nakamura, K. and Harashima, K., "Elucidation of the Erwinia uredovora carotenoid biosynthetic pathway by functional analysis of gene products expressed in Escherichia coli", J. Bacteriol., 172, pp. 6704–6712, 1990; and Japanese Unexamined Patent Publication No. 3-58786) to BstEII digestion, Klenow enzyme treatment and a ligase reaction, the crtX gene was deactivated by a frameshift. Then, a 6.0 kb Asp718(KpnI)-EcoRI fragment was cut out which contains the crtE, crtY, crtI and crtB genes necessary for β-carotene production. This fragment was inserted into the EcoRV site of E. coli vector pACYC184 (obtained from ATCC 37033) to thereby obtain the plasmid of interest (designated as pACCAR16Δ crtX). The E. coli carrying this pACCAR16Δ crtX exhibits chloramphenicol resistance and can produce β-carotene.

(2) Screening for the keto group-introducing enzyme gene

It is considered that ketocarotenoids are biosynthesized in Haematococcus pluvialis via β-carotene (see Britton, G., "Biosynthesis of carotenoids", Plant Pigments, Goodwin, W. (ed.), London, Academic Press, 1988, pp. 133–182). Then, utilizing the phenomenon that E. coli JM101 carrying the plasmid pACCAR16Δ crtX described above produces β-carotene (yellow), the cDNA expression library obtained above was introduced to this E. coli. Subsequently, the E. coli carrying the keto group-introducing enzyme gene was screened from the color change in the resultant transformants. It was expected that, when keto groups were introduced and canthaxanthin (one of ketocarotenoids) began to be produced, the color of E. coli would change from the yellow of β-carotene to the red of canthaxanthin.

First, using the method described in Molecular Cloning (2nd edition): Cold Spring Harbor Laboratory, 1.21–1.41 (1989), competent cells of E. coli JM101 carrying pACCAR16Δ crtX were prepared.

Figure 10:
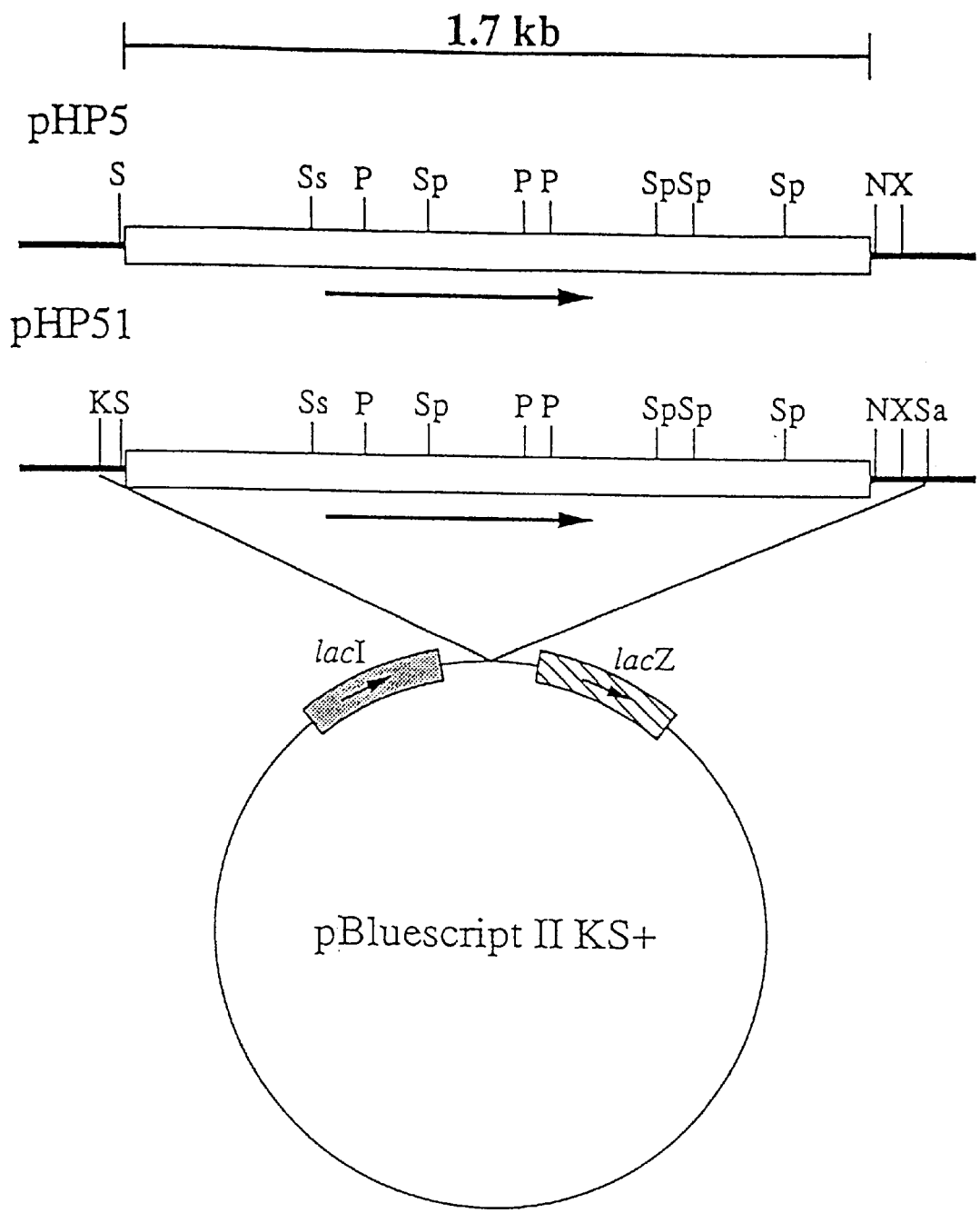
FIG. 10 shows two plasmids pHP5 and pHP51 each containing the keto group-introducing enzyme gene (bkt) from the green alga *Haematococcus pluvialis* NIES-144.

Then, to 1 ml of these competent cells, 100 ng of the cDNA expression library was introduced, and the screening was conducted for about 40,000 transformants to thereby isolate one strain which was reddish and slightly different from others in color tone. (The pigment of this strain was identified as canthaxanthin in Example 7.) In addition, the cDNA expression plasmid carried by this strain was designated as pHP5. The constitution of plasmid pHP5 is shown in FIG. 10.

[Example 7]

Determination of the Base Sequence of the Keto Group-Introducing Enzyme Gene

A Haematococcus pluvialis-derived 1.7 kb cDNA inserted into pPH5 was cut out with the restriction enzymes SalI and XbaI. This fragment was inserted into the SalI/XbaI site of both E. coli vector pBluescript II KS+ and E. coli vector pBluescript II SK+ to thereby obtain two plasmids (pHP51 and pHP52). Of these plasmids, the restriction map of pHP51 is shown in FIG. 10. pHP51 and pHP52 are different in the direction of the above cDNA fragment inserted therein. In the former plasmid, the cDNA fragment undergoes the read-through of the lac promoter and in the latter the cDNA fragment does not.

Using the obtained plasmids pHP51 and pHP52, deletion variants having various lengths of deletions were prepared by the following procedures and their base sequences were determined. pHP51 was digested with SacI and XbaI, and pHP52 with KpnI and SalI. Then, phenol/chloroform extraction was carried out and the DNA was recovered by ethanol precipitation. Each DNA was dissolved in 100 μl of ExoIII buffer (50 mM Tris-HCl, 100 mM NaCl, 5 mM MgCl$_2$, 10 mM 2-mercaptoethanol, pH 8.0) and, after the addition of 180 units of ExoIII nuclease thereto, kept at 37° C. By sampling a 10 μl reaction solution in every 30 seconds, each sample was transfered into a tube containing 10 μl of MB buffer (40 mM NaCl, 2 mM ZnCl$_2$, 10% glycerol, pH 4.5) located on ice. After the completion of the sampling, the 10 tubes obtained was kept at 65° C. for 10 minutes to deactivate enzymes. Then, 5 units of mung bean nuclease was added thereto and kept at 37° C. for 30 minutes. After the completion of the reaction, 10 kinds of DNA fragments having varying degrees of deletions were recovered per one plasmid by agarose gel electrophoresis. The recovered DNAs were blunt-ended with Klenow enzyme and subjected to ligation reaction at 16° C. overnight, to thereby transform E. coli DH5α. Plasmids were prepared for the resultant various clones, and sequence reactions were performed by using a fluorescent primer cycle sequence kit manufactured by Applied Biosystems. Then, the base sequence of each plasmid was determined with an automatic sequencer.

The thus determined base sequence consisting of 1677 bp is shown in FIGS. 4 and 5 (SEQ ID NO: 1). As a result of search for open reading frames, 3 open reading frames have been found which individually have a ribosome binding site at the upstream of the initiation codon that is necessary for the expression in *E. coli*. These three frames are shown individually as A–D in FIG. 1 (SEQ ID NO: 3 in the sequence listing), as B–D in FIG. 2 (SEQ ID NO: 5) and as C–D in FIG. 3 (SEQ ID NO: 7). As demonstrated in Example 8 infra, a shorter polypeptide than C14 D loses the enzyme activity in *E. coli*, and thus it is considered that no initiation codon exists downstream of C. Therefore, the region locating downstream of C in FIG. 3 was excluded from the search for open reading frames as described above.

[EXAMPLE 8]

Determination of the Initiation Codon for the Keto Group-Introducing Enzyme Gene FIG. 11 shows the base sequence for an upstream portion of the open reading frames described above (bases 1–480 of SEQ ID NO:1). There are 5 potential initiation codon sites (base positions 168–170, 189–191, 264–266, 348–350 and 423–425 (SEQ ID NO:1); these sites are enclosed with boxes in FIG. 11). The bases at positions 168, 189 and 264 shown in the initiation codons in FIG. 11 correspond to positions A in FIG. 1, B in FIG. 2 and C in FIG. 3, respectively. In order to determine the necessary minimum region as a functional protein, deletion variants of pHP51 were prepared in substantially the same manner as in Example 5, to thereby obtain several plasmids wherein the upstream region was deleted. FIG. 11 shows the number of each of these deletion plasmids and their upstream ends. These plasmids were individually introduced into the *E. coli* JM101 carrying pACCAR16Δ crtX as described in Example 6 and the pigments produced were identified. As a result, *E. coli* cells carrying deletion plasmids Nos. 30, 27, 31, 37 and 12 were observed to produce canthaxanthin, but those cells carrying deletion plasmids Nos. 10, 6 and 38 were not observed to produce it. With respect to the deletion plasmid No. 12 which lacks A of the initiation codon ATG at base positions 264–266, this ATG became GTG when a deletion variant was produced. Since *E. coli* can recognize even GTG as an initiation codon, it is considered that the synthesis of a peptide is starting from the initiation codon at this position. Therefore, it has become clear that a polypeptide chain encoded by the open reading frame starting from the initiation codon at positions 264–266 [C–D in FIG. 3 (as shown in SEQ ID NO: 7)] sufficiently exhibits the enzyme activity of keto group introduction.

[EXAMPLE 9]

Identification of a Ketocarotenoid Pigment (1) Identification of canthaxanthin

β-carotene producing *E. coli* JM101 into which pHP5 or pHP51 has been introduced (*E. coli* pACCAR16Δ crtX, pHP5 or pHP51) (presenting an orange color) was cultured in 2 liters of 2YT medium (1.6% tryptone, 1% yeast extract, 0.5% NaCl) containing 150 μg/ml ampicillin (Ap, Meiji Seika Kaisha), 30 μg/ml chloramphenicol (Cm, Sankyo, Co.), 1 mM IPTG, 7 mg $FeSO_4.7H_2O$ and 9.3 mg $Na_2.EDTA$ at 30° C. for 24–30 hours. Cells harvested from the culture were extracted with 300 ml of acetone, and after concentration, extracted twice with 200 ml of chloroform/methanol (9/1) followed by concentration/drying/caking. The resultant material was dissolved in a small amount of chloroform/methanol (9/1) and subjected to thin layer chromatography (TLC) using a preparatory silica gel plate (Merck) and developing with chloroform/methanol (50/1). By means of this TLC, spots were separated into three with Rf values of 0.53, 0.78 and 1. The most dark red pigment (of Rf value 0.53) representing 75% of the total pigments extracted was recovered from the TLC plate. This red pigment was further dissolved in a small amount of chloroform/methanol (9/1), applied to Sephadex LH-20 column chromatography (15×300 mm) and developed and eluted with chloroform/methanol (9/1) or chloroform/methanol (1/1), to thereby obtain 2 mg of a pure pigment. All of the ultraviolet-visible spectrum, $^1H$-NMR, FD-MS spectrum (m/e 564) and mobility on silica gel TLC [the Rf value was 0.53 when developed with chloroform/methanol (50/1)] of this substance agreed with those of a standard canthaxanthin product (BASF), and thus this substance was identified as canthaxanthin (for the structural formula, see FIG. 8).

Further, a red pigment (having an Rf value of 0.78 on TLC) which represented 10% of the total pigments initially extracted was recovered from the TLC plate and dissolved in a small amount of methanol. In view of the ultraviolet-visible spectrum, mobility on silica gel TLC [the Rf value was 0.78 when developed with chloroform/methanol (50/1)] and mobility on HPLC using Novapack HR6μ $C_{18}$ (3.9×300 mm) (Waters) [RT was 16 minutes when developed with acetonitrile/methanol/2-propanol (90/6/4) at a flow rate of 1.0 ml/min] of this pigment, it was believed to be echinenone (for the structural formula, see FIG. 8).

Then, a yellow pigment (having an Rf value of 1 on TLC) which represented the remaining 15% of the total pigments initially extracted was scraped from the TLC plate and dissolved in a small amount of methanol. Since the ultraviolet-visible spectrum and mobility on HPLC using Novapack HR6μ $C_{18}$ (3.9×300 mm) (Waters) [RT was 62 minutes when developed with acetonitrile/methanol/2-propanol (90/6/4) at a flow rate of 1.0 ml/mon] of this pigment agreed with those of a β-carotene standard product (all trans type, Sigma), this substance was found to be an unreacted β-carotene (for the structural formula, see FIG. 8).

(2) Identification of astaxanthin and 4-ketozeaxanthin

A zeaxanthin-producing *E. coli* was prepared as follows. Briefly, plasmid pCAR25 having all of the carotenoid synthesis genes from *Er. uredovora* (Misawa, N., Nakagawa, M., Kobayashi, K., Yamano, S., Izawa, Y., Nakamura, K. and Harashima, K., "Elucidation of the *Erwinia uredovora* carotenoid biosynthetic pathway by functional analysis of gene products expressed in *Escherichia coli*", J. Bacteriol., 172, pp. 6704–6712, 1990; and Japanese Unexamined Patent Publication No. 3-58786) was subjected to BstEII digestion, Klenow fragment treatment and a ligase reaction to thereby deactivate the crtX gene by a frameshift. Then, a 6.5 kb Asp718(KpnI)-EcoRI fragment was cut out which contains the crtE, crtB, crtI, crtY and crtZ genes necessary for zeaxanthin production. This fragment was inserted into the EcoRV site of *E. coli* vector pACYC184 to thereby obtain the plasmid of interest (designated as pACCAR25Δ crtX).

The zeaxanthin-producing *E. coli* JM101 into which pHP5 or pHP51 has been introduced (*E. coli* pACCAR25Δ crtX, pHP5 or pHP51) (presenting an orange color) was cultured in 2 liters of 2YT medium (1.6% tryptone, 1% yeast extract, 0.5% NaCl) containing 150 μ/ml Ap, 30 μg/ml Cm, 1 mM IPTG, 7 mg $FeSO_4.7H_2O$ and 9.3 mg $Na_4.EDTA$ at 30° C. for 24–30 hours. Cells harvested from the culture were extracted with 300 ml of acetone, and after concentration, extracted twice with 200 ml of chloroform/ methanol (9/1) followed by concentration/drying/caking. The resultant material was dissolved in a small amount of chloroform/methanol (9/1) and subjected to thin layer chromatography (TLC) using a preparatory silica gel TLC plate (Merck) and developing with chloroform/methanol (15/1). By means of this TLC, the initial orange pigment was separated into 3 major spots with Rf values of 0.40, 0.54 and 0.72. These pigments were recovered from the TLC plate, dissolved separately in a small amount of chloroform/methanol (9/1), applied to Sephadex LH-20 column chromatography (15×300 mm) and developed and eluted with chloroform/methanol (9/1) or methanol, to thereby obtain three pure pigments in amounts of about 1 mg, 1 mg and 2 mg.

A pigment having an Rf value of 0.72 which represented about half of the total pigments extracted was found to have the same planar structure as that of astaxanthin in view of the results of its ultraviolet-visible spectrum, $^1$H-NMR and FD-MS spectrum (m/e 596). Then, this pigment was dissolved in diethyl ether:2-propanol:ethanol (5:5:2) and measured the CD spectrum. As a result, this substance was found to take a steric structure of 3S,3'S. Therefore, this substance was identified as astaxanthin (for the structural formula, see FIG. 8). Another pigment of Rf 0.54 was identified as 4-ketozeaxanthin (for the structural formula, see FIG. 8) in view of the results of its ultraviolet-visible spectrum, $^1$H-NMR, FD-MS spectrum (m/e 582) and mobility on silica gel TLC [the Rf value was 0.54 when developed with chloroform/methanol (15/1)]. With respect to the pigment having an Rf value of 0.40, its ultraviolet-visible spectrum, mobility on silica gel TLC [the Rf value was 0.40 when developed with chloroform/methanol (50/1)] and mobility on HPLC using Novapack HR6$\mu$ C$_{18}$ (3.9×300 mm) (Waters) [RT was 6.5 minutes when developed with acetonitrile/methano ½-propanol (90/6/4) at a flow rate of 1.0 ml/min] all agreed with those of a zeaxanthin standard product (BASF). Therefore, this substance was found to be an unreacted zeaxanthin (for the structural formula, see FIG. 8).

From so far described, the functions of the keto group-introducing enzyme gene can be considered as follows.

Figure 6:
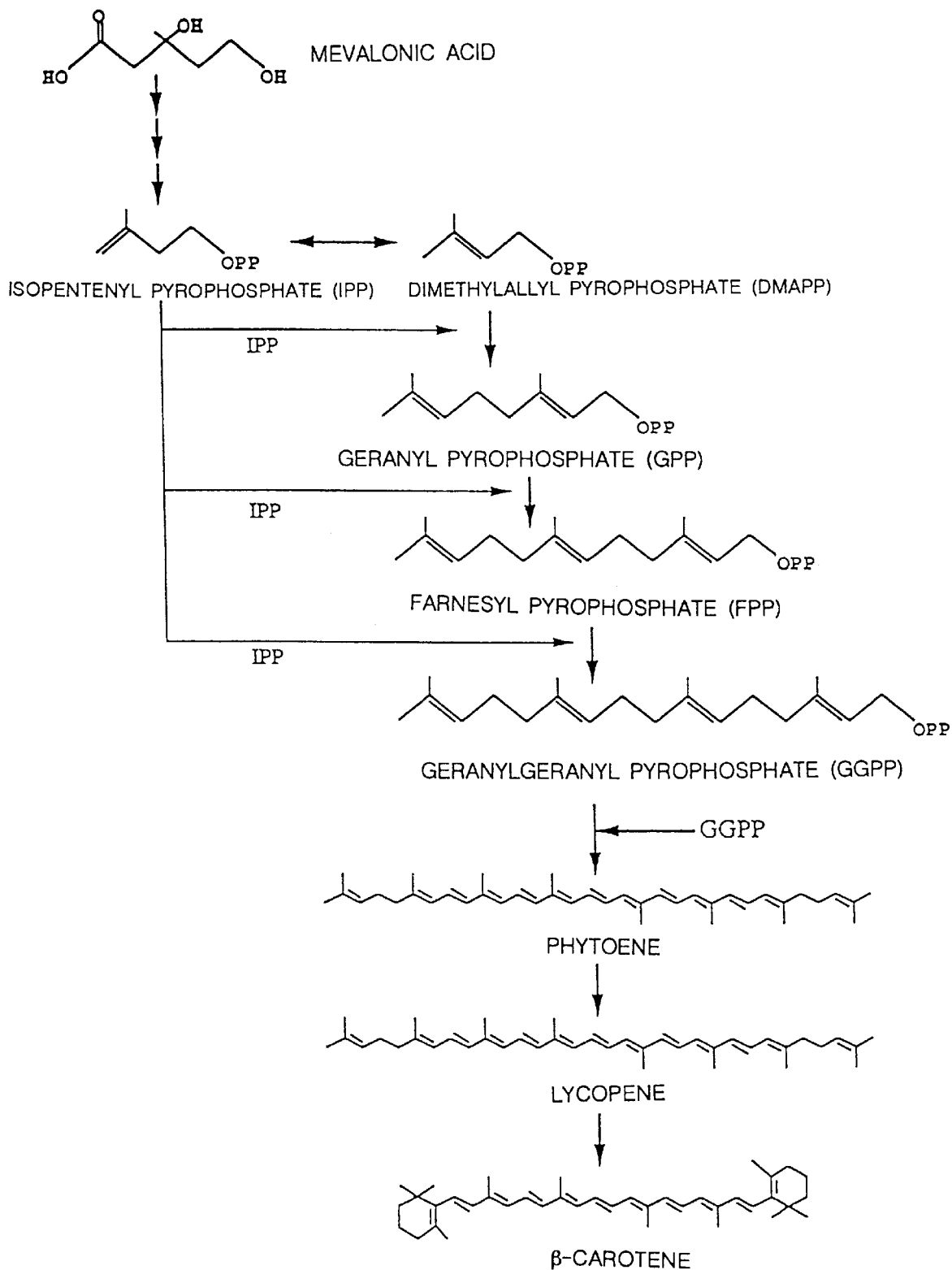
FIG. 6 shows a carotenoid biosynthesis pathway up to β-carotene.
Figure 7:
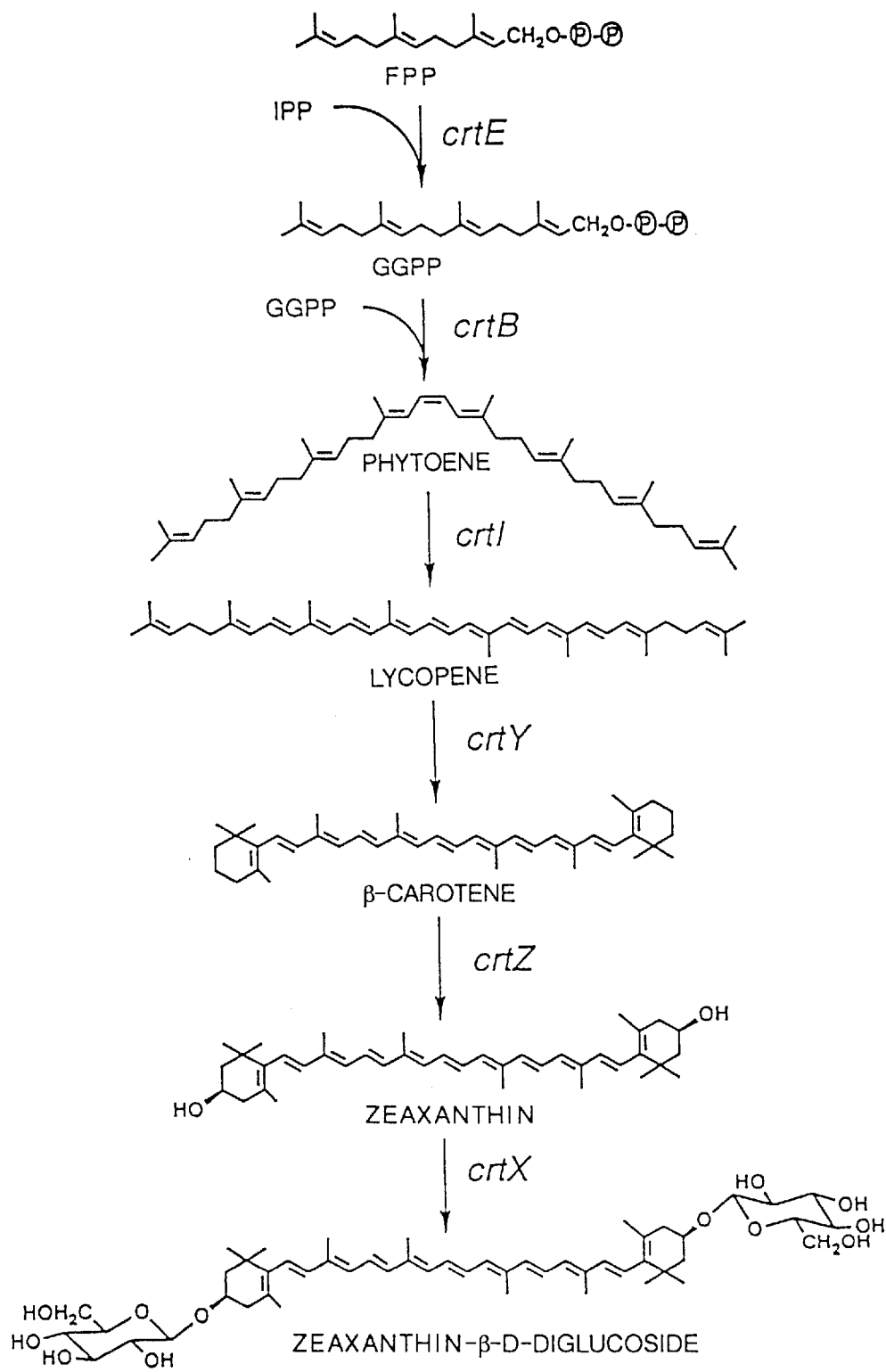
FIG. 7 shows the carotenoid biosynthesis pathway of the non-photosynthetic *Erwinia uredovora* as well as the functions of carotenoid synthesis genes.
Figure 8:
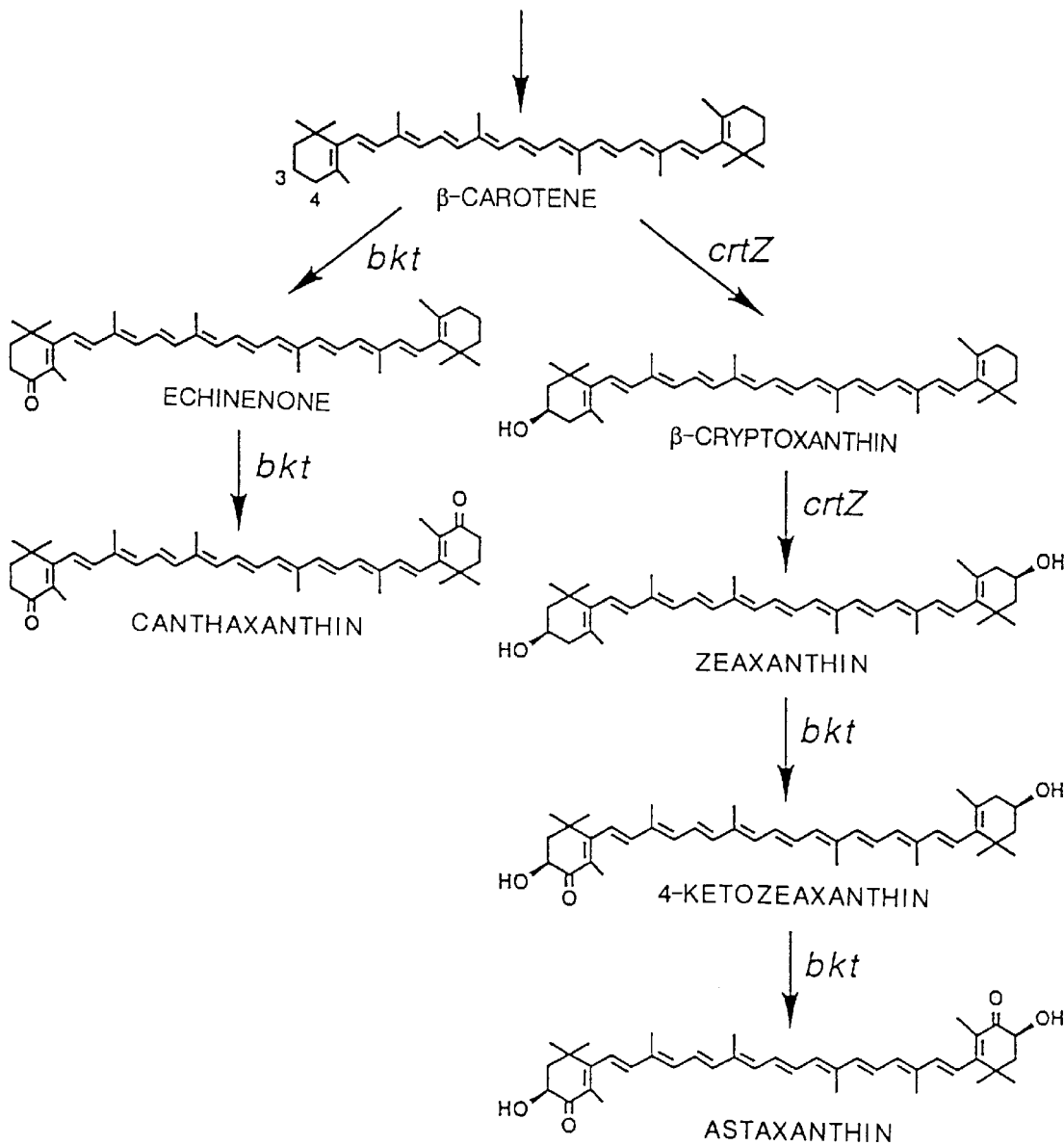
FIG. 8 shows the functions of the keto group-introducing enzyme gene (bkt) from the green alga *Haematococcus pluvialis* NIES-144, the functions of the hydroxyl group-introducing enzyme gene (crtZ) from the non-photosynthetic *Erwinia uredovora* and major ketocarotenoid biosynthesis pathways.

From (1) of Example 9, it is clear that the Haematococcus-derived keto group-introducing enzyme gene (bkt) is coding for a keto group-introducing enzyme (β-carotene ketolase) which catalyzes the conversion of β-carotene (a substrate) to canthaxanthin via echinenone (see FIG. 8). This shows that one enzyme, BKT, converts the methylene groups at positions 4 and 4' of a β-ionone ring directly to keto groups. No enzyme having such a function has been known so far. In addition, from (2) of Example 9, it is clear that the Haematococcus-derived bkt gene is also coding for another keto group-introducing enzyme (zeaxanthin ketolase) which catalyzes the conversion of zeaxanthin (a substrate) to astaxanthin via 4-ketozeaxanthin (see FIG. 8). This shows that one enzyme, BKT, converts the methylene groups at positions 4 and 4' of 3- and 3'-hydroxy-β-ionone rings directly to keto groups. No enzyme having such a function has been known so far either. Accordingly, it can be said that the Haematococcus-derived keto group-introducing enzyme gene bkt is coding for an β-ionone or 3-hydroxy-β-ionone ring keto group-introducing enzyme (β-ionone or 3-hydroxy-β-ionone ring ketolase) which converts the methylene group at position 4 (4') to a keto group directly, regardless of whether a hydroxyl group is added to position 3 (3'). Not limited in β-ionone rings or 3-hydroxy-β-ionone rings, there has been reported no finding so far that one enzyme converts a methylene group to a keto group directly.

Figure 9:
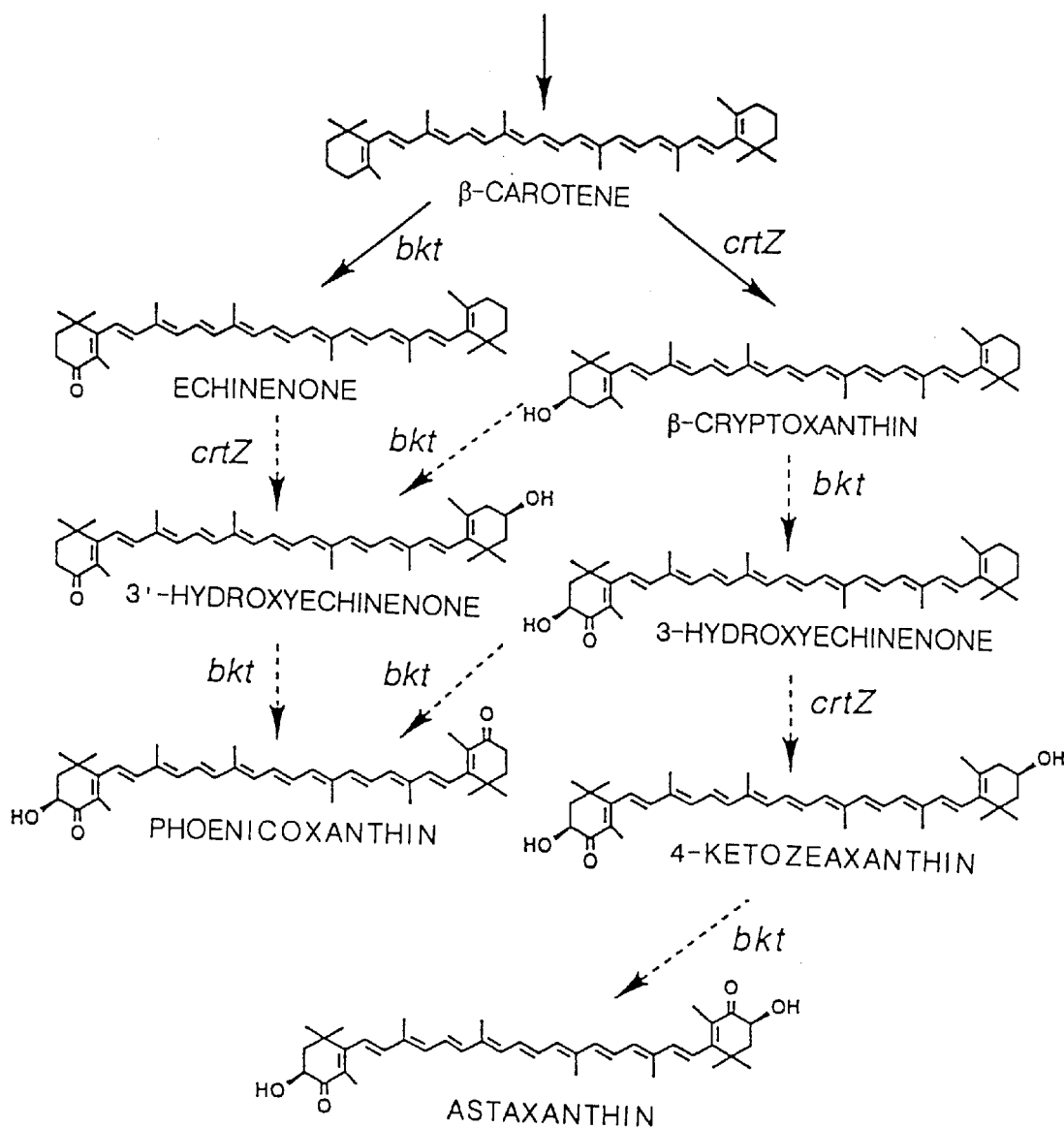
FIG. 9 shows the functions of the keto group-introducing enzyme gene (bkt) from the green alga *Haematococcus pluvialis* NIES-144, the functions of the hydroxyl group-introducing enzyme gene (crtZ) from the non-photosynthetic *Erwinia uredovora* and minor ketocarotenoid biosynthesis pathways.

On the other hand, according to the researches of the present inventors using carotenoid synthesis genes from the bacteria Erwinia present in plants and the photosynthetic bacteria Rhodobacter, it has become clear that, generally, a carotenoid biosynthesis enzyme recognizes only one half of the carotenoid molecule which is a substrate and acts on it. For example, crtY which is a lycopene ring formation enzyme gene recognizes by one half of the lycopene molecule and makes the ring formation. Therefore, by using the phytoene desaturase gene crtI from Rhodobacter, it is possible to allow *E. coli* to produce neurosporene instead of lycopene. And when the produced neurosporene is treated with the erwinia-derived crtY, the crtY gene product recognizes only the half structure of a neurosporene molecule which is common with lycopene and, as a result, β-zeacarotene is produced which is circulized by half (see Linden, H., Misawa, N., Chamovitz, D., Pecker, I., Hirschberg, J. and Sandmann, G., "Functional complementation in *Escherichia coli* of different phytoene desaturase genes and analysis of accumulated carotenes", Z. Naturforsch., 46c, pp. 1045–1051, 1991). In addition, in the present invention also, when β-carotene was treated with BKT, first echinenone is synthesized wherein one keto group is introduced, and when zeaxanthin is treated with BKT, first 4-ketozeaxanthin is synthesized wherein one keto group is introduced. This can be considered that BKT recognizes one half of a substrate molecule and introduces a keto group at position 4. On the other hand, the *E. coli* carrying the Erwinia-derived crtE, crtB, crtI, crtY and crtZ genes produces zeaxanthin as described above, but β-cryptoxanthin wherein one hydroxyl group is introduced into β-carotene can also be detected in the products as an intermediary metabolite. This means that, if BKT is present there, 3'-hydroxyechinenone and 3-hydroxyechinenone can be produced with the β-cryptoxanthin as a substrate. In addition, it can be also considered that BKT further acts on these substances produced to thereby synthesize phoenicoxanthin. This time, we have not achieved the identification of these substances in cultures, because under the conditions employed for this time it seems that these substances are present only in extremely small amounts. In fact, in the typical astaxanthin-producing microorganism *Phaffia rhodozyma* which is comparable with Haematococcus, 3-hydroxyechinenone and phoenicoxanthin are detected as intermediary metabolites of astaxanthin (Andrewes, A. G., Phaff, H. J. and Starr, M. P., "Carotenoids of *Phaffia rhodozyma*, a redpigmented fermenting yeast", Phytochemistry, 15, pp. 1003–1007, 1976). From so far described, it is possible to consider that there are the minor metabolic pathways shown in FIG. 9 other than the major astaxanthin metabolic pathway shown in FIG. 8.

[EXAMPLE 10]

Southern Analysis of the Genomic DNA of the other Green Algae Haematococcus

It was examined as to whether some regions showing homology with bkt's isolated in the chromosomes of the other green algae Haematococcus. In the same manner as described in Example 2 for preparing the total DNA of *Haematococcus pluvialis* NIES-144, the total DNAs of *Haematococcus lucustris* UTEX 294 and *Haematococcus lucustris* C-392 were prepared. The resultant DNAs together with the total DNA of *H. pluvialis* NIES-144 were digested with the restriction enzyme HindIII, PstI or XbaI and separated by agarose gel electrophoresis. The separated DNA fragments were denatured with an alkali solution of 0.5 N NaOH/1.5 M NaCl, and then transferred to a nylon membrane overnight. The nylon membrane which had adsorbed DNA was soaked in a hybridization solution (6×Denhardt, 5×SSC, 0.2% SDS, 100 μg/ml ssDNA) to carry out a prehybridization for 4 hours at 55 ° C. Then, a 1.7 kb DNA fragment of bkt gene was labelled by using Megaprime™ DNA labelling system (Amersham) and [α-$^{32}$P]dCTP (up to 110 TBq/mmol) and added to the prehybridization solution described above to thereby carry out a hybridization for 16 hours at 55° C. After the hybridization, the reaction solution was washed with 2×SSC and 0.1% SDS at 60° C. for 1 hour and subjected to autoradiography to detect signals indicating homology. As a result, with respect to *Haematococcus pluvialis* NIES-144, strong signals were obtained at positions 15kb, 10 kb and 1.9 kb in HindIII digest, 6.1 kb, 3.3 kb, 2.8 kb, 2.3 kb, 2.0 kb, 1.4 kb and 0.8 kb in PstI digest and 5.1 kb in XbaI digest. With respect to *Haematococcus lucustris* UTEX 294, strong signals were obtained at positions 15 kb, 7.7 kb and 1.9 kb in HindIII digest, 10 kb, 5.0 kb, 4.0 kb, 3.4 kb, 2.9 kb, 1.5 kb and 0.82 kb in PstI digest and only at a position more than 20 kb in XbaI digest. With respect to *Haematococcus lucustris* C-392, strong signals were obtained at positions 15kb, 12 kb and 1.9 kb in HindIII digest, 6.5 kb, 3.0 kb, 2.3 kb, 2.0 kb, 1.4 kb and 0.8 kb in PstI digest and 5. 3 kb in XbaI digest (see FIG. 12).

INDUSTRIAL APPLICABILITY

By introducing into a microorganism such as *E. coli* as a foreign gene the DNA of the invention coding for an enzyme which convert the methylene group at position 4 of β-ionone ring to a keto group and allowing the microorganism to express the DNA, it has become possible to render a microorganism such as *E. coli* an ability to biosynthesize ketocarotenoids such as astaxanthin, 4-ketozeaxanthin, canthaxanthin, echinenone and other keto group-containing ketocarotenoids. By using the microorganism such as *E. coli* which has been rendered the ability to biosynthesize keto group-containing ketocarotenoids, it is possible to produce keto group-containing ketocarotenoids in large quantity with small labor and at low cost.

What is claimed is:

1. An isolated and purified DNA comprising a base sequence coding for a polypeptide obtained from an organism selected from the group consisting of Haematococcus and crustaceans, said polypeptide having an enzyme activity to convert the methylene group at position 4 of a β-ionone ring in a compound containing a β-ionine ring to a keto group.

2. A DNA comprising a base sequence that hybridizes with the DNA of claim 1, in hybridization solution comprising 6×Denhart, 5×SSC, 0.2% SDS, 100 μg/ml ssDNA at 55° C. followed by washing with 2×SSC, 0.1% SDS at 60° C. and which comprises a base sequence coding for a polypeptide having an enzyme activity to convert the methylene group at position 4 of a β-ionone ring in a compound containing a β-ionone ring to a keto group.

3. The DNA of claim 1, wherein said polypeptide comprises an amino acid sequence selected from the group consisting of SEQ ID NO:4, SEQ ID NO:6 and SEQ ID NO:8.

4. The DNA of claim 3, wherein the sequence coding for the polypeptide comprising the amino acid sequence of SEQ ID NO: 4 is shown as SEQ ID NO: 3.

5. The DNA of claim 3, wherein said base sequence coding for the polypeptide comprising the amino acid sequence as shown in SEQ ID NO:6 of the sequence listing is the base sequence as shown in SEQ ID NO:5 of the sequence listing.

6. The DNA of claim 3, wherein said base sequence coding for the polypeptide comprising the amino acid sequence as shown in SEQ ID NO:8 of the sequence listing is the base sequence as shown in SEQ ID NO:7 of the sequence listing.

7. The DNA of claim 1, wherein said compound containing β-ionone rings is β-carotene.

8. The DNA of claim 1, wherein a hydrogen atom at position 3 of said β-ionone ring is replaced with a hydroxyl group.

9. The DNA of claim 8, wherein the compound containing said β-ionone ring is zeaxanthin.

10. The plasmid pHP51 having Accession Number FERM BP-4757.

11. A recombinant vector comprising the DNA of claim 1.

12. A host cell into which the DNA of claim 1 has been introduced.

13. A method for producing a ketocarotenoid, comprising culturing a host cell of claim 12 in a medium comprising a compound containing a β-ionone ring and collecting a ketocarotenoid from the culture.

14. The method of claim 13, wherein said ketocarotenoid is selected from the group consisting of echinenone, canthaxanthin, 4-ketozeaxanthin, and astaxanthin.

15. The method of claim 13, wherein said microorganism is a bacterium or a yeast.

16. The method of claim 13, wherein said DNA sequence is obtained from the green alga Haematococcus.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 1677 base pairs
      (B) TYPE: nucleic acid
      (C) STRANDEDNESS: double
      (D) TOPOLOGY: linear (ix) FEATURE:
      (A) NAME/KEY: CDS
      (B) LOCATION: 168..1127

(ix) FEATURE:
      (A) NAME/KEY: mat_peptide
      (B) LOCATION: 168..1127

(xi) SEQUENCE DESCRIPTION: SEQ ID NO:1:

```
CGGGGCAACT CAAGAAATTC AACAGCTGCA AGCGCGCCCC AGCCTCACAG CGCCAAGTGA         60

GCTATCGACG TGGTTGTGAG CGCTCGACGT GGTCCACTGA CGGGCCTGTG AGCCTCTGCG        120

CTCCGTCCTC TGCCAAATCT CGCGTCGGGG CCTGCCTAAG TCGAAGA ATG CAC GTC         176
                                                  Met His Val
                                                    1

GCA TCG GCA CTA ATG GTC GAG CAG AAA GGC AGT GAG GCA GCT GCT TCC         224
Ala Ser Ala Leu Met Val Glu Gln Lys Gly Ser Glu Ala Ala Ala Ser
      5                  10                  15

AGC CCA GAC GTC TTG AGA GCG TGG GCG ACA CAG TAT CAC ATG CCA TCC         272
Ser Pro Asp Val Leu Arg Ala Trp Ala Thr Gln Tyr His Met Pro Ser
 20                  25                  30                  35

GAG TCG TCA GAC GCA GCT CGT CCT GCG CTA AAG CAC GCC TAC AAA CCT         320
Glu Ser Ser Asp Ala Ala Arg Pro Ala Leu Lys His Ala Tyr Lys Pro
                 40                  45                  50

CCA GCA TCT GAC GCC AAG GGC ATC ACG ATG GCG CTG ACC ATC ATT GGC         368
Pro Ala Ser Asp Ala Lys Gly Ile Thr Met Ala Leu Thr Ile Ile Gly
             55                  60                  65

ACC TGG ACC GCA GTG TTT TTA CAC GCA ATA TTT CAA ATC AGG CTA CCG         416
Thr Trp Thr Ala Val Phe Leu His Ala Ile Phe Gln Ile Arg Leu Pro
         70                  75                  80
```

```
ACA TCC ATG GAC CAG CTT CAC TGG TTG CCT GTG TCC GAA GCC ACA GCC      464
Thr Ser Met Asp Gln Leu His Trp Leu Pro Val Ser Glu Ala Thr Ala
         85                  90                  95

CAG CTT TTG GGC GGA AGC AGC AGC CTA CTG CAC ATC GCT GCA GTC TTC      512
Gln Leu Leu Gly Gly Ser Ser Ser Leu Leu His Ile Ala Ala Val Phe
100                 105                 110                 115

ATT GTA CTT GAG TTC CTG TAC ACT GGT CTA TTC ATC ACC ACA CAT GAC      560
Ile Val Leu Glu Phe Leu Tyr Thr Gly Leu Phe Ile Thr Thr His Asp
                120                 125                 130

GCA ATG CAT GGC ACC ATA GCT TTG AGG CAC AGG CAG CTC AAT GAT CTC      608
Ala Met His Gly Thr Ile Ala Leu Arg His Arg Gln Leu Asn Asp Leu
            135                 140                 145

CTT GGC AAC ATC TGC ATA TCA CTG TAC GCC TGG TTT GAC TAC AGC ATG      656
Leu Gly Asn Ile Cys Ile Ser Leu Tyr Ala Trp Phe Asp Tyr Ser Met
        150                 155                 160

CTG CAT CGC AAG CAC TGG GAG CAC CAC AAC CAT ACT GGC GAA GTG GGG      704
Leu His Arg Lys His Trp Glu His His Asn His Thr Gly Glu Val Gly
    165                 170                 175

AAA GAC CCT GAC TTC CAC AAG GGA AAT CCC GGC CTT GTC CCC TGG TTC      752
Lys Asp Pro Asp Phe His Lys Gly Asn Pro Gly Leu Val Pro Trp Phe
180                 185                 190                 195

GCC AGC TTC ATG TCC AGC TAC ATG TCC CTG TGG CAG TTT GCC CGG CTG      800
Ala Ser Phe Met Ser Ser Tyr Met Ser Leu Trp Gln Phe Ala Arg Leu
                200                 205                 210

GCA TGG TGG GCA GTG GTG ATG CAA ATG CTG GGG GCG CCC ATG GCA AAT      848
Ala Trp Trp Ala Val Val Met Gln Met Leu Gly Ala Pro Met Ala Asn
            215                 220                 225

CTC CTA GTC TTC ATG GCT GCA GCC CCA ATC TTG TCA GCA TTC CGC CTC      896
Leu Leu Val Phe Met Ala Ala Ala Pro Ile Leu Ser Ala Phe Arg Leu
        230                 235                 240

TTC TAC TTC GGC ACT TAC CTG CCA CAC AAG CCT GAG CCA GGC CCT GCA      944
Phe Tyr Phe Gly Thr Tyr Leu Pro His Lys Pro Glu Pro Gly Pro Ala
    245                 250                 255

GCA GGC TCT CAG GTG ATG GCC TGG TTC AGG GCC AAG ACA AGT GAG GCA      992
Ala Gly Ser Gln Val Met Ala Trp Phe Arg Ala Lys Thr Ser Glu Ala
260                 265                 270                 275

TCT GAT GTG ATG AGT TTC CTG ACA TGC TAC CAC TTT GAC CTG CAC TGG     1040
Ser Asp Val Met Ser Phe Leu Thr Cys Tyr His Phe Asp Leu His Trp
                280                 285                 290

GAG CAC CAC AGG TGG CCC TTT GCC CCC TGG TGG CAG CTG CCC CAC TGC     1088
Glu His His Arg Trp Pro Phe Ala Pro Trp Trp Gln Leu Pro His Cys
            295                 300                 305

CGC CGC CTG TCC GGG CGT GGC CTG GTG CCT GCC TTG GCA TGACCTGGTC      1137
Arg Arg Leu Ser Gly Arg Gly Leu Val Pro Ala Leu Ala
        310                 315                 320

CCTCCGCTGG TGACCCAGCG TCTGCACAAG AGTGTCATGC TACAGGGTGC TGCGGCCAGT   1197

GGCAGCGCAG TGCACTCTCA GCCTGTATGG GGCTACCGCT GTGCCACTGA GCACTGGGCA   1257

TGCCACTGAG CACTGGGCGT GCTACTGAGC AATGGGCGTG CTACTGAGCA ATGGGCGTGC   1317

TACTGACAAT GGGCGTGCTA CTGGGGTCTG GCAGTGGCTA GGATGGAGTT TGATGCATTC   1377

AGTAGCGGTG CCAACGTCA TGTGGATGGT GGAAGTGCTG AGGGGTTTAG GCAGCCGGCA    1437

TTTGAGAGGG CTAAGTTATA AATCGCATGC TGCTCATGCG CACATATCTG CACACAGCCA   1497

GGGAAATCCC TTCGAGAGTG ATTATGGGAC ACTTGTATTG GTTTCGTGCT ATTGTTTTAT   1557

TCAGCAGCAG TACTTAGTGA GGGTGAGAGC AGGGTGGTGA GAGTGGAGTG AGTGAGTATG   1617

AACCTGGTCA GCGAGGTGAA CAGCCTGTAA TGAATGACTC TGTCTAAAAA AAAAAAAAAA   1677
```

(2) INFORMATION FOR SEQ ID NO:2:

(i) SEQUENCE CHARACTERISTICS:
        (A) LENGTH: 320 amino acids
        (B) TYPE: amino acid
        (D) TOPOLOGY: linear (ii) MOLECULE TYPE: protein (xi) SEQUENCE DESCRIPTION: SEQ ID NO:2:

```
Met His Val Ala Ser Ala Leu Met Val Glu Gln Lys Gly Ser Glu Ala
 1               5                  10                  15

Ala Ala Ser Ser Pro Asp Val Leu Arg Ala Trp Ala Thr Gln Tyr His
                20                  25                  30

Met Pro Ser Glu Ser Ser Asp Ala Ala Arg Pro Ala Leu Lys His Ala
            35                  40                  45

Tyr Lys Pro Pro Ala Ser Asp Ala Lys Gly Ile Thr Met Ala Leu Thr
50                  55                  60

Ile Ile Gly Thr Trp Thr Ala Val Phe Leu His Ala Ile Phe Gln Ile
65                  70                  75                  80

Arg Leu Pro Thr Ser Met Asp Gln Leu His Trp Leu Pro Val Ser Glu
                85                  90                  95

Ala Thr Ala Gln Leu Leu Gly Gly Ser Ser Ser Leu Leu His Ile Ala
            100                 105                 110

Ala Val Phe Ile Val Leu Glu Phe Leu Tyr Thr Gly Leu Phe Ile Thr
        115                 120                 125

Thr His Asp Ala Met His Gly Thr Ile Ala Leu Arg His Arg Gln Leu
130                 135                 140

Asn Asp Leu Leu Gly Asn Ile Cys Ile Ser Leu Tyr Ala Trp Phe Asp
145                 150                 155                 160

Tyr Ser Met Leu His Arg Lys His Trp Glu His His Asn His Thr Gly
                165                 170                 175

Glu Val Gly Lys Asp Pro Asp Phe His Lys Gly Asn Pro Gly Leu Val
            180                 185                 190

Pro Trp Phe Ala Ser Phe Met Ser Ser Tyr Met Ser Leu Trp Gln Phe
        195                 200                 205

Ala Arg Leu Ala Trp Trp Ala Val Val Met Gln Met Leu Gly Ala Pro
210                 215                 220

Met Ala Asn Leu Leu Val Phe Met Ala Ala Pro Ile Leu Ser Ala
225                 230                 235                 240

Phe Arg Leu Phe Tyr Phe Gly Thr Tyr Leu Pro His Lys Pro Glu Pro
                245                 250                 255

Gly Pro Ala Ala Gly Ser Gln Val Met Ala Trp Phe Arg Ala Lys Thr
            260                 265                 270

Ser Glu Ala Ser Asp Val Met Ser Phe Leu Thr Cys Tyr His Phe Asp
        275                 280                 285

Leu His Trp Glu His His Arg Trp Pro Phe Ala Pro Trp Trp Gln Leu
290                 295                 300

Pro His Cys Arg Arg Leu Ser Gly Arg Gly Leu Val Pro Ala Leu Ala
305                 310                 315                 320
```

(2) INFORMATION FOR SEQ ID NO:3:

(i) SEQUENCE CHARACTERISTICS:
        (A) LENGTH: 963 base pairs
        (B) TYPE: nucleic acid
        (C) STRANDEDNESS: double
        (D) TOPOLOGY: linear (ix) FEATURE:
    (A) NAME/KEY: CDS
    (B) LOCATION: 1..960

(ix) FEATURE:
    (A) NAME/KEY: mat_peptide
    (B) LOCATION: 1..960

(xi) SEQUENCE DESCRIPTION: SEQ ID NO:3:

```
ATG CAC GTC GCA TCG GCA CTA ATG GTC GAG CAG AAA GGC AGT GAG GCA      48
Met His Val Ala Ser Ala Leu Met Val Glu Gln Lys Gly Ser Glu Ala
 1               5                  10                  15

GCT GCT TCC AGC CCA GAC GTC TTG AGA GCG TGG GCG ACA CAG TAT CAC      96
Ala Ala Ser Ser Pro Asp Val Leu Arg Ala Trp Ala Thr Gln Tyr His
                20                  25                  30

ATG CCA TCC GAG TCG TCA GAC GCA GCT CGT CCT GCG CTA AAG CAC GCC     144
Met Pro Ser Glu Ser Ser Asp Ala Ala Arg Pro Ala Leu Lys His Ala
            35                  40                  45

TAC AAA CCT CCA GCA TCT GAC GCC AAG GGC ATC ACG ATG GCG CTG ACC     192
Tyr Lys Pro Pro Ala Ser Asp Ala Lys Gly Ile Thr Met Ala Leu Thr
50                  55                  60

ATC ATT GGC ACC TGG ACC GCA GTG TTT TTA CAC GCA ATA TTT CAA ATC     240
Ile Ile Gly Thr Trp Thr Ala Val Phe Leu His Ala Ile Phe Gln Ile
 65                  70                  75                  80

AGG CTA CCG ACA TCC ATG GAC CAG CTT CAC TGG TTG CCT GTG TCC GAA     288
Arg Leu Pro Thr Ser Met Asp Gln Leu His Trp Leu Pro Val Ser Glu
                85                  90                  95

GCC ACA GCC CAG CTT TTG GGC GGA AGC AGC AGC CTA CTG CAC ATC GCT     336
Ala Thr Ala Gln Leu Leu Gly Gly Ser Ser Ser Leu Leu His Ile Ala
            100                 105                 110

GCA GTC TTC ATT GTA CTT GAG TTC CTG TAC ACT GGT CTA TTC ATC ACC     384
Ala Val Phe Ile Val Leu Glu Phe Leu Tyr Thr Gly Leu Phe Ile Thr
        115                 120                 125

ACA CAT GAC GCA ATG CAT GGC ACC ATA GCT TTG AGG CAC AGG CAG CTC     432
Thr His Asp Ala Met His Gly Thr Ile Ala Leu Arg His Arg Gln Leu
    130                 135                 140

AAT GAT CTC CTT GGC AAC ATC TGC ATA TCA CTG TAC GCC TGG TTT GAC     480
Asn Asp Leu Leu Gly Asn Ile Cys Ile Ser Leu Tyr Ala Trp Phe Asp
145                 150                 155                 160

TAC AGC ATG CTG CAT CGC AAG CAC TGG GAG CAC CAC AAC CAT ACT GGC     528
Tyr Ser Met Leu His Arg Lys His Trp Glu His His Asn His Thr Gly
                165                 170                 175

GAA GTG GGG AAA GAC CCT GAC TTC CAC AAG GGA AAT CCC GGC CTT GTC     576
Glu Val Gly Lys Asp Pro Asp Phe His Lys Gly Asn Pro Gly Leu Val
            180                 185                 190

CCC TGG TTC GCC AGC TTC ATG TCC AGC TAC ATG TCC CTG TGG CAG TTT     624
Pro Trp Phe Ala Ser Phe Met Ser Ser Tyr Met Ser Leu Trp Gln Phe
        195                 200                 205

GCC CGG CTG GCA TGG TGG GCA GTG GTG ATG CAA ATG CTG GGG GCG CCC     672
Ala Arg Leu Ala Trp Trp Ala Val Val Met Gln Met Leu Gly Ala Pro
    210                 215                 220

ATG GCA AAT CTC CTA GTC TTC ATG GCT GCA GCC CCA ATC TTG TCA GCA     720
Met Ala Asn Leu Leu Val Phe Met Ala Ala Ala Pro Ile Leu Ser Ala
225                 230                 235                 240

TTC CGC CTC TTC TAC TTC GGC ACT TAC CTG CCA CAC AAG CCT GAG CCA     768
Phe Arg Leu Phe Tyr Phe Gly Thr Tyr Leu Pro His Lys Pro Glu Pro
                245                 250                 255

GGC CCT GCA GCA GGC TCT CAG GTG ATG GCC TGG TTC AGG GCC AAG ACA     816
Gly Pro Ala Ala Gly Ser Gln Val Met Ala Trp Phe Arg Ala Lys Thr
            260                 265                 270

AGT GAG GCA TCT GAT GTG ATG AGT TTC CTG ACA TGC TAC CAC TTT GAC     864
Ser Glu Ala Ser Asp Val Met Ser Phe Leu Thr Cys Tyr His Phe Asp
```

```
                  275                 280                 285
CTG CAC TGG GAG CAC CAC AGG TGG CCC TTT GCC CCC TGG TGG CAG CTG          912
Leu His Trp Glu His His Arg Trp Pro Phe Ala Pro Trp Trp Gln Leu
    290                 295                 300

CCC CAC TGC CGC CGC CTG TCC GGG CGT GGC CTG GTG CCT GCC TTG GCA          960
Pro His Cys Arg Arg Leu Ser Gly Arg Gly Leu Val Pro Ala Leu Ala
305                 310                 315                 320

TGA                                                                       963

(2) INFORMATION FOR SEQ ID NO:4:

(i) SEQUENCE CHARACTERISTICS:
        (A) LENGTH: 320 amino acids
        (B) TYPE: amino acid
        (D) TOPOLOGY: linear (ii) MOLECULE TYPE: protein (xi) SEQUENCE DESCRIPTION: SEQ ID NO:4:

Met His Val Ala Ser Ala Leu Met Val Glu Gln Lys Gly Ser Glu Ala
  1               5                  10                  15

Ala Ala Ser Ser Pro Asp Val Leu Arg Ala Trp Ala Thr Gln Tyr His
             20                  25                  30

Met Pro Ser Glu Ser Ser Asp Ala Ala Arg Pro Ala Leu Lys His Ala
         35                  40                  45

Tyr Lys Pro Pro Ala Ser Asp Ala Lys Gly Ile Thr Met Ala Leu Thr
     50                  55                  60

Ile Ile Gly Thr Trp Thr Ala Val Phe Leu His Ala Ile Phe Gln Ile
 65                  70                  75                  80

Arg Leu Pro Thr Ser Met Asp Gln Leu His Trp Leu Pro Val Ser Glu
                 85                  90                  95

Ala Thr Ala Gln Leu Leu Gly Gly Ser Ser Leu Leu His Ile Ala
            100                 105                 110

Ala Val Phe Ile Val Leu Glu Phe Leu Tyr Thr Gly Leu Phe Ile Thr
        115                 120                 125

Thr His Asp Ala Met His Gly Thr Ile Ala Leu Arg His Arg Gln Leu
    130                 135                 140

Asn Asp Leu Leu Gly Asn Ile Cys Ile Ser Leu Tyr Ala Trp Phe Asp
145                 150                 155                 160

Tyr Ser Met Leu His Arg Lys His Trp Glu His His Asn His Thr Gly
                165                 170                 175

Glu Val Gly Lys Asp Pro Asp Phe His Lys Gly Asn Pro Gly Leu Val
            180                 185                 190

Pro Trp Phe Ala Ser Phe Met Ser Ser Tyr Met Ser Leu Trp Gln Phe
        195                 200                 205

Ala Arg Leu Ala Trp Trp Ala Val Val Met Gln Met Leu Gly Ala Pro
    210                 215                 220

Met Ala Asn Leu Leu Val Phe Met Ala Ala Pro Ile Leu Ser Ala
225                 230                 235                 240

Phe Arg Leu Phe Tyr Phe Gly Thr Tyr Leu Pro His Lys Pro Glu Pro
                245                 250                 255

Gly Pro Ala Ala Gly Ser Gln Val Met Ala Trp Phe Arg Ala Lys Thr
            260                 265                 270

Ser Glu Ala Ser Asp Val Met Ser Phe Leu Thr Cys Tyr His Phe Asp
        275                 280                 285

Leu His Trp Glu His His Arg Trp Pro Phe Ala Pro Trp Trp Gln Leu
    290                 295                 300
```

```
Pro His Cys Arg Arg Leu Ser Gly Arg Gly Leu Val Pro Ala Leu Ala
305                 310                 315                 320
```

(2) INFORMATION FOR SEQ ID NO:5:

(i) SEQUENCE CHARACTERISTICS:
        (A) LENGTH: 942 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..939

(ix) FEATURE:
        (A) NAME/KEY: mat_peptide
        (B) LOCATION: 1..939

(xi) SEQUENCE DESCRIPTION: SEQ ID NO:5:

```
ATG GTC GAG CAG AAA GGC AGT GAG GCA GCT GCT TCC AGC CCA GAC GTC      48
Met Val Glu Gln Lys Gly Ser Glu Ala Ala Ala Ser Ser Pro Asp Val
1               5                   10                  15

TTG AGA GCG TGG GCG ACA CAG TAT CAC ATG CCA TCC GAG TCG TCA GAC      96
Leu Arg Ala Trp Ala Thr Gln Tyr His Met Pro Ser Glu Ser Ser Asp
            20                  25                  30

GCA GCT CGT CCT GCG CTA AAG CAC GCC TAC AAA CCT CCA GCA TCT GAC     144
Ala Ala Arg Pro Ala Leu Lys His Ala Tyr Lys Pro Pro Ala Ser Asp
        35                  40                  45

GCC AAG GGC ATC ACG ATG GCG CTG ACC ATC ATT GGC ACC TGG ACC GCA     192
Ala Lys Gly Ile Thr Met Ala Leu Thr Ile Ile Gly Thr Trp Thr Ala
    50                  55                  60

GTG TTT TTA CAC GCA ATA TTT CAA ATC AGG CTA CCG ACA TCC ATG GAC     240
Val Phe Leu His Ala Ile Phe Gln Ile Arg Leu Pro Thr Ser Met Asp
65                  70                  75                  80

CAG CTT CAC TGG TTG CCT GTG TCC GAA GCC ACA GCC CAG CTT TTG GGC     288
Gln Leu His Trp Leu Pro Val Ser Glu Ala Thr Ala Gln Leu Leu Gly
                85                  90                  95

GGA AGC AGC AGC CTA CTG CAC ATC GCT GCA GTC TTC ATT GTA CTT GAG     336
Gly Ser Ser Ser Leu Leu His Ile Ala Ala Val Phe Ile Val Leu Glu
            100                 105                 110

TTC CTG TAC ACT GGT CTA TTC ATC ACC ACA CAT GAC GCA ATG CAT GGC     384
Phe Leu Tyr Thr Gly Leu Phe Ile Thr Thr His Asp Ala Met His Gly
        115                 120                 125

ACC ATA GCT TTG AGG CAC AGG CAG CTC AAT GAT CTC CTT GGC AAC ATC     432
Thr Ile Ala Leu Arg His Arg Gln Leu Asn Asp Leu Leu Gly Asn Ile
    130                 135                 140

TGC ATA TCA CTG TAC GCC TGG TTT GAC TAC AGC ATG CTG CAT CGC AAG     480
Cys Ile Ser Leu Tyr Ala Trp Phe Asp Tyr Ser Met Leu His Arg Lys
145                 150                 155                 160

CAC TGG GAG CAC CAC AAC CAT ACT GGC GAA GTG GGG AAA GAC CCT GAC     528
His Trp Glu His His Asn His Thr Gly Glu Val Gly Lys Asp Pro Asp
                165                 170                 175

TTC CAC AAG GGA AAT CCC GGC CTT GTC CCC TGG TTC GCC AGC TTC ATG     576
Phe His Lys Gly Asn Pro Gly Leu Val Pro Trp Phe Ala Ser Phe Met
            180                 185                 190

TCC AGC TAC ATG TCC CTG TGG CAG TTT GCC CGG CTG GCA TGG TGG GCA     624
Ser Ser Tyr Met Ser Leu Trp Gln Phe Ala Arg Leu Ala Trp Trp Ala
        195                 200                 205

GTG GTG ATG CAA ATG CTG GGG GCG CCC ATG GCA AAT CTC CTA GTC TTC     672
Val Val Met Gln Met Leu Gly Ala Pro Met Ala Asn Leu Leu Val Phe
    210                 215                 220

ATG GCT GCA GCC CCA ATC TTG TCA GCA TTC CGC CTC TTC TAC TTC GGC     720
```

```
Met Ala Ala Ala Pro Ile Leu Ser Ala Phe Arg Leu Phe Tyr Phe Gly
225                 230                 235                 240

ACT TAC CTG CCA CAC AAG CCT GAG CCA GGC CCT GCA GCA GGC TCT CAG          768
Thr Tyr Leu Pro His Lys Pro Glu Pro Gly Pro Ala Ala Gly Ser Gln
                245                 250                 255

GTG ATG GCC TGG TTC AGG GCC AAG ACA AGT GAG GCA TCT GAT GTG ATG          816
Val Met Ala Trp Phe Arg Ala Lys Thr Ser Glu Ala Ser Asp Val Met
            260                 265                 270

AGT TTC CTG ACA TGC TAC CAC TTT GAC CTG CAC TGG GAG CAC CAC AGG          864
Ser Phe Leu Thr Cys Tyr His Phe Asp Leu His Trp Glu His His Arg
        275                 280                 285

TGG CCC TTT GCC CCC TGG TGG CAG CTG CCC CAC TGC CGC CGC CTG TCC          912
Trp Pro Phe Ala Pro Trp Trp Gln Leu Pro His Cys Arg Arg Leu Ser
    290                 295                 300

GGG CGT GGC CTG GTG CCT GCC TTG GCA TGA                                  942
Gly Arg Gly Leu Val Pro Ala Leu Ala
305                 310
```

(2) INFORMATION FOR SEQ ID NO:6:

(i) SEQUENCE CHARACTERISTICS:
        (A) LENGTH: 313 amino acids
        (B) TYPE: amino acid
        (D) TOPOLOGY: linear (ii) MOLECULE TYPE: protein (xi) SEQUENCE DESCRIPTION: SEQ ID NO:6:

```
Met Val Glu Gln Lys Gly Ser Glu Ala Ala Ser Ser Pro Asp Val
1               5                   10                  15

Leu Arg Ala Trp Ala Thr Gln Tyr His Met Pro Ser Glu Ser Ser Asp
                20                  25                  30

Ala Ala Arg Pro Ala Leu Lys His Ala Tyr Lys Pro Pro Ala Ser Asp
            35                  40                  45

Ala Lys Gly Ile Thr Met Ala Leu Thr Ile Ile Gly Thr Trp Thr Ala
        50                  55                  60

Val Phe Leu His Ala Ile Phe Gln Ile Arg Leu Pro Thr Ser Met Asp
65                  70                  75                  80

Gln Leu His Trp Leu Pro Val Ser Glu Ala Thr Ala Gln Leu Leu Gly
                85                  90                  95

Gly Ser Ser Ser Leu Leu His Ile Ala Ala Val Phe Ile Val Leu Glu
            100                 105                 110

Phe Leu Tyr Thr Gly Leu Phe Ile Thr Thr His Asp Ala Met His Gly
        115                 120                 125

Thr Ile Ala Leu Arg His Arg Gln Leu Asn Asp Leu Leu Gly Asn Ile
    130                 135                 140

Cys Ile Ser Leu Tyr Ala Trp Phe Asp Tyr Ser Met Leu His Arg Lys
145                 150                 155                 160

His Trp Glu His His Asn His Thr Gly Glu Val Gly Lys Asp Pro Asp
                165                 170                 175

Phe His Lys Gly Asn Pro Gly Leu Val Pro Trp Phe Ala Ser Phe Met
            180                 185                 190

Ser Ser Tyr Met Ser Leu Trp Gln Phe Ala Arg Leu Ala Trp Trp Ala
        195                 200                 205

Val Val Met Gln Met Leu Gly Ala Pro Met Ala Asn Leu Leu Val Phe
    210                 215                 220

Met Ala Ala Ala Pro Ile Leu Ser Ala Phe Arg Leu Phe Tyr Phe Gly
225                 230                 235                 240
```

```
Thr Tyr Leu Pro His Lys Pro Glu Pro Gly Pro Ala Ala Gly Ser Gln
            245                 250                 255

Val Met Ala Trp Phe Arg Ala Lys Thr Ser Glu Ala Ser Asp Val Met
            260                 265                 270

Ser Phe Leu Thr Cys Tyr His Phe Asp Leu His Trp Glu His His Arg
            275                 280                 285

Trp Pro Phe Ala Pro Trp Trp Gln Leu Pro His Cys Arg Arg Leu Ser
            290                 295                 300

Gly Arg Gly Leu Val Pro Ala Leu Ala
305                 310
```

(2) INFORMATION FOR SEQ ID NO:7:

(i) SEQUENCE CHARACTERISTICS:
        (A) LENGTH: 867 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..864

(ix) FEATURE:
        (A) NAME/KEY: mat_peptide
        (B) LOCATION: 1..864

(xi) SEQUENCE DESCRIPTION: SEQ ID NO:7:

```
ATG CCA TCC GAG TCG TCA GAC GCA GCT CGT CCT GCG CTA AAG CAC GCC     48
Met Pro Ser Glu Ser Ser Asp Ala Ala Arg Pro Ala Leu Lys His Ala
 1               5                  10                  15

TAC AAA CCT CCA GCA TCT GAC GCC AAG GGC ATC ACG ATG GCG CTG ACC     96
Tyr Lys Pro Pro Ala Ser Asp Ala Lys Gly Ile Thr Met Ala Leu Thr
            20                  25                  30

ATC ATT GGC ACC TGG ACC GCA GTG TTT TTA CAC GCA ATA TTT CAA ATC    144
Ile Ile Gly Thr Trp Thr Ala Val Phe Leu His Ala Ile Phe Gln Ile
        35                  40                  45

AGG CTA CCG ACA TCC ATG GAC CAG CTT CAC TGG TTG CCT GTG TCC GAA    192
Arg Leu Pro Thr Ser Met Asp Gln Leu His Trp Leu Pro Val Ser Glu
    50                  55                  60

GCC ACA GCC CAG CTT TTG GGC GGA AGC AGC AGC CTA CTG CAC ATC GCT    240
Ala Thr Ala Gln Leu Leu Gly Gly Ser Ser Ser Leu Leu His Ile Ala
65                  70                  75                  80

GCA GTC TTC ATT GTA CTT GAG TTC CTG TAC ACT GGT CTA TTC ATC ACC    288
Ala Val Phe Ile Val Leu Glu Phe Leu Tyr Thr Gly Leu Phe Ile Thr
                85                  90                  95

ACA CAT GAC GCA ATG CAT GGC ACC ATA GCT TTG AGG CAC AGG CAG CTC    336
Thr His Asp Ala Met His Gly Thr Ile Ala Leu Arg His Arg Gln Leu
            100                 105                 110

AAT GAT CTC CTT GGC AAC ATC TGC ATA TCA CTG TAC GCC TGG TTT GAC    384
Asn Asp Leu Leu Gly Asn Ile Cys Ile Ser Leu Tyr Ala Trp Phe Asp
        115                 120                 125

TAC AGC ATG CTG CAT CGC AAG CAC TGG GAG CAC CAC AAC CAT ACT GGC    432
Tyr Ser Met Leu His Arg Lys His Trp Glu His His Asn His Thr Gly
    130                 135                 140

GAA GTG GGG AAA GAC CCT GAC TTC CAC AAG GGA AAT CCC GGC CTT GTC    480
Glu Val Gly Lys Asp Pro Asp Phe His Lys Gly Asn Pro Gly Leu Val
145                 150                 155                 160

CCC TGG TTC GCC AGC TTC ATG TCC AGC TAC ATG TCC CTG TGG CAG TTT    528
Pro Trp Phe Ala Ser Phe Met Ser Ser Tyr Met Ser Leu Trp Gln Phe
                165                 170                 175

GCC CGG CTG GCA TGG TGG GCA GTG GTG ATG CAA ATG CTG GGG GCG CCC    576
Ala Arg Leu Ala Trp Trp Ala Val Val Met Gln Met Leu Gly Ala Pro
```

-continued

```
              180                 185                 190
ATG GCA AAT CTC CTA GTC TTC ATG GCT GCA GCC CCA ATC TTG TCA GCA       624
Met Ala Asn Leu Leu Val Phe Met Ala Ala Ala Pro Ile Leu Ser Ala
        195                 200                 205

TTC CGC CTC TTC TAC TTC GGC ACT TAC CTG CCA CAC AAG CCT GAG CCA       672
Phe Arg Leu Phe Tyr Phe Gly Thr Tyr Leu Pro His Lys Pro Glu Pro
    210                 215                 220

GGC CCT GCA GCA GGC TCT CAG GTG ATG GCC TGG TTC AGG GCC AAG ACA       720
Gly Pro Ala Ala Gly Ser Gln Val Met Ala Trp Phe Arg Ala Lys Thr
225                 230                 235                 240

AGT GAG GCA TCT GAT GTG ATG AGT TTC CTG ACA TGC TAC CAC TTT GAC       768
Ser Glu Ala Ser Asp Val Met Ser Phe Leu Thr Cys Tyr His Phe Asp
                245                 250                 255

CTG CAC TGG GAG CAC CAC AGG TGG CCC TTT GCC CCC TGG TGG CAG CTG       816
Leu His Trp Glu His His Arg Trp Pro Phe Ala Pro Trp Trp Gln Leu
            260                 265                 270

CCC CAC TGC CGC CGC CTG TCC GGG CGT GGC CTG GTG CCT GCC TTG GCA       864
Pro His Cys Arg Arg Leu Ser Gly Arg Gly Leu Val Pro Ala Leu Ala
        275                 280                 285

TGA                                                                   867
```

(2) INFORMATION FOR SEQ ID NO:8:

(i) SEQUENCE CHARACTERISTICS:
        (A) LENGTH: 288 amino acids
        (B) TYPE: amino acid
        (D) TOPOLOGY: linear (ii) MOLECULE TYPE: protein (xi) SEQUENCE DESCRIPTION: SEQ ID NO:8:

```
Met Pro Ser Glu Ser Ser Asp Ala Ala Arg Pro Ala Leu Lys His Ala
 1               5                  10                  15

Tyr Lys Pro Pro Ala Ser Asp Ala Lys Gly Ile Thr Met Ala Leu Thr
            20                  25                  30

Ile Ile Gly Thr Trp Thr Ala Val Phe Leu His Ala Ile Phe Gln Ile
        35                  40                  45

Arg Leu Pro Thr Ser Met Asp Gln Leu His Trp Leu Pro Val Ser Glu
    50                  55                  60

Ala Thr Ala Gln Leu Leu Gly Gly Ser Ser Ser Leu Leu His Ile Ala
65                  70                  75                  80

Ala Val Phe Ile Val Leu Glu Phe Leu Tyr Thr Gly Leu Phe Ile Thr
                85                  90                  95

Thr His Asp Ala Met His Gly Thr Ile Ala Leu Arg His Arg Gln Leu
            100                 105                 110

Asn Asp Leu Leu Gly Asn Ile Cys Ile Ser Leu Tyr Ala Trp Phe Asp
        115                 120                 125

Tyr Ser Met Leu His Arg Lys Trp Glu His Asn His Thr Gly
    130                 135                 140

Glu Val Gly Lys Asp Pro Asp Phe His Lys Gly Asn Pro Gly Leu Val
145                 150                 155                 160

Pro Trp Phe Ala Ser Phe Met Ser Ser Tyr Met Ser Leu Trp Gln Phe
                165                 170                 175

Ala Arg Leu Ala Trp Trp Ala Val Val Met Gln Met Leu Gly Ala Pro
            180                 185                 190

Met Ala Asn Leu Leu Val Phe Met Ala Ala Ala Pro Ile Leu Ser Ala
        195                 200                 205

Phe Arg Leu Phe Tyr Phe Gly Thr Tyr Leu Pro His Lys Pro Glu Pro
```

```
           210                 215                 220
Gly Pro Ala Ala Gly Ser Gln Val Met Ala Trp Phe Arg Ala Lys Thr
225                 230                 235                 240

Ser Glu Ala Ser Asp Val Met Ser Phe Leu Thr Cys Tyr His Phe Asp
                245                 250                 255

Leu His Trp Glu His His Arg Trp Pro Phe Ala Pro Trp Trp Gln Leu
                260                 265                 270

Pro His Cys Arg Arg Leu Ser Gly Arg Gly Leu Val Pro Ala Leu Ala
                275                 280                 285
```

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:9:

GGNTGGGGNT GGCAYAARTC NCAYCA                                      26

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:10:

CANCGYTGRT GNACNAGNCC RTCRTG                                      26

(2) INFORMATION FOR SEQ ID NO:11:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:11:

GCRTASATRA ANCCRAARCT NACRCA                                      26